(12) United States Patent
Tokhtuev et al.

(10) Patent No.: US 8,008,080 B2
(45) Date of Patent: Aug. 30, 2011

(54) VALVE ANALYTICAL SYSTEM

(75) Inventors: Eugene Tokhtuev, Duluth, MN (US); Christopher Owen, Duluth, MN (US); William Christensen, Hibbing, MN (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 12/565,520

(22) Filed: Sep. 23, 2009

(65) Prior Publication Data

US 2011/0070654 A1   Mar. 24, 2011

(51) Int. Cl.
*G01N 35/00* (2006.01)

(52) U.S. Cl. ............ 436/45; 422/99; 422/100; 422/63; 422/64; 422/65; 436/180; 251/142

(58) Field of Classification Search ............ 422/99–100, 422/63–65; 436/45, 180; 251/142
See application file for complete search history.

(56) References Cited

U.S. PATENT DOCUMENTS

| | | | |
|---|---|---|---|
| 4,068,528 A | | 1/1978 | Gundelfinger |
| 4,520,108 A | * | 5/1985 | Yoshida et al. |
| 5,792,621 A | * | 8/1998 | Verostko et al. |
| 5,988,236 A | | 11/1999 | Fawcett |
| 6,162,602 A | | 12/2000 | Gautsch |
| 6,600,558 B2 | * | 7/2003 | Ueno et al. |
| 6,656,159 B2 | * | 12/2003 | Flaherty |
| 6,692,457 B2 | * | 2/2004 | Flaherty |
| 6,699,218 B2 | * | 3/2004 | Flaherty et al. |
| 6,706,527 B2 | | 3/2004 | Szecsody |
| 6,748,975 B2 | | 6/2004 | Hartshorne |
| 6,749,587 B2 | * | 6/2004 | Flaherty |
| 7,016,462 B1 | * | 3/2006 | Keville et al. |
| 7,153,473 B2 | | 12/2006 | Ericson et al. |
| 7,186,383 B2 | | 3/2007 | Webster |
| 7,198,956 B2 | | 4/2007 | Uffenheimer et al. |
| 7,314,718 B1 | | 1/2008 | Dasgupta et al. |
| 7,361,157 B2 | | 4/2008 | Yamazaki |
| 2007/0202608 A1 | | 8/2007 | Uffenheimer et al. |
| 2008/0185102 A1 | | 8/2008 | Van Kessel |
| 2009/0150106 A1 | | 6/2009 | Erickson et al. |

OTHER PUBLICATIONS

FIAlab, "Sequential Injection Lab-On-Valve Manifold, retrieved from http://www.flowinjection.com/SIA_Addons/SIA_LOV.aspx on Sep. 29, 2009, 1 page.
International Search Report and Written Opinion, dated May 30, 2011 for PCT Application No. PCT/IB2010/054245 6 pages).

* cited by examiner

*Primary Examiner* — Jyoti Nagpaul
(74) *Attorney, Agent, or Firm* — Fredrickson & Byron, PA

(57) ABSTRACT

A lab on a valve analytical system includes a rotary sample preparation assembly having a stator and a rotor. The rotor includes a plurality of integral syringe pumps which can be aligned with passages formed within the stator. The stator passages can be connected with fluid inlet connector which connect the sample preparation assembly with fluid sources, and fluid outlet connectors which connect the sample preparation assembly with one or more wet chemical analytical devices. Some embodiments can include a mixer and optical sensor connected with the fluid outlets. One or more drive motors can be used to control simultaneous actuation of one or more of the syringe pumps, thereby providing for simultaneous delivery of metered volumes of fluid.

7 Claims, 18 Drawing Sheets

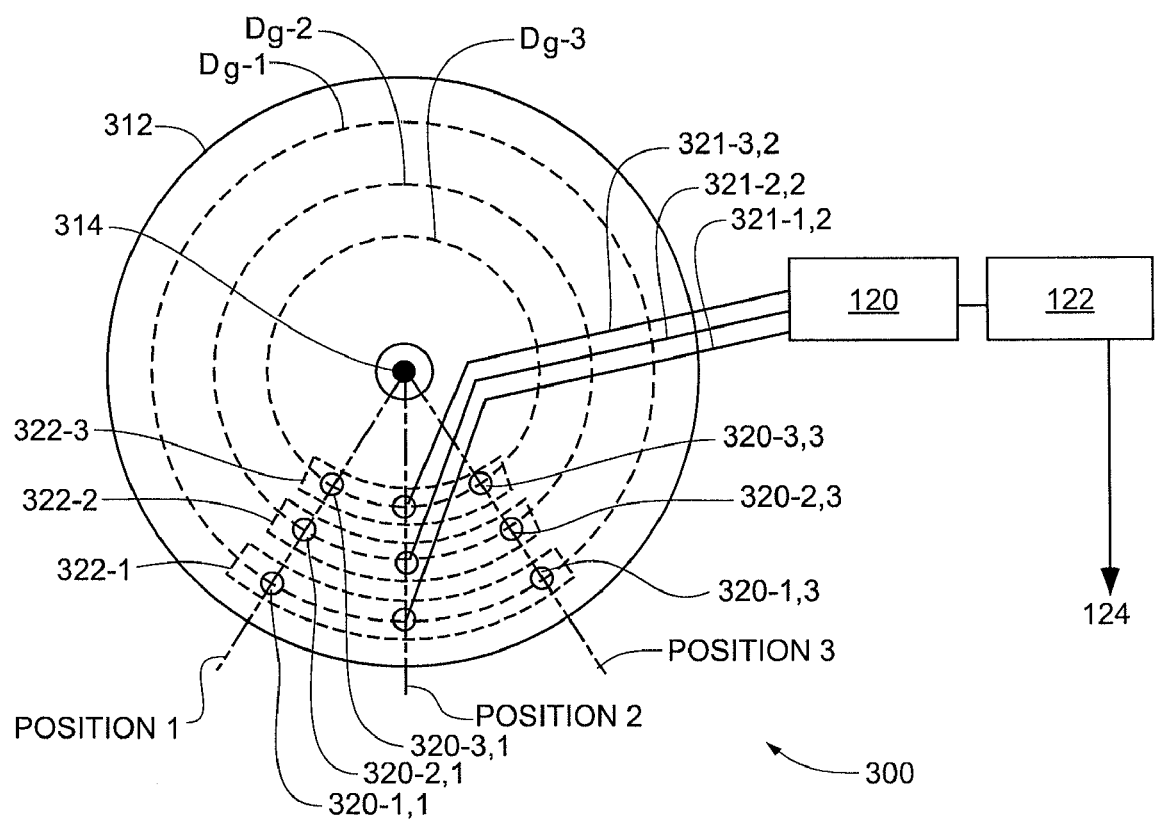

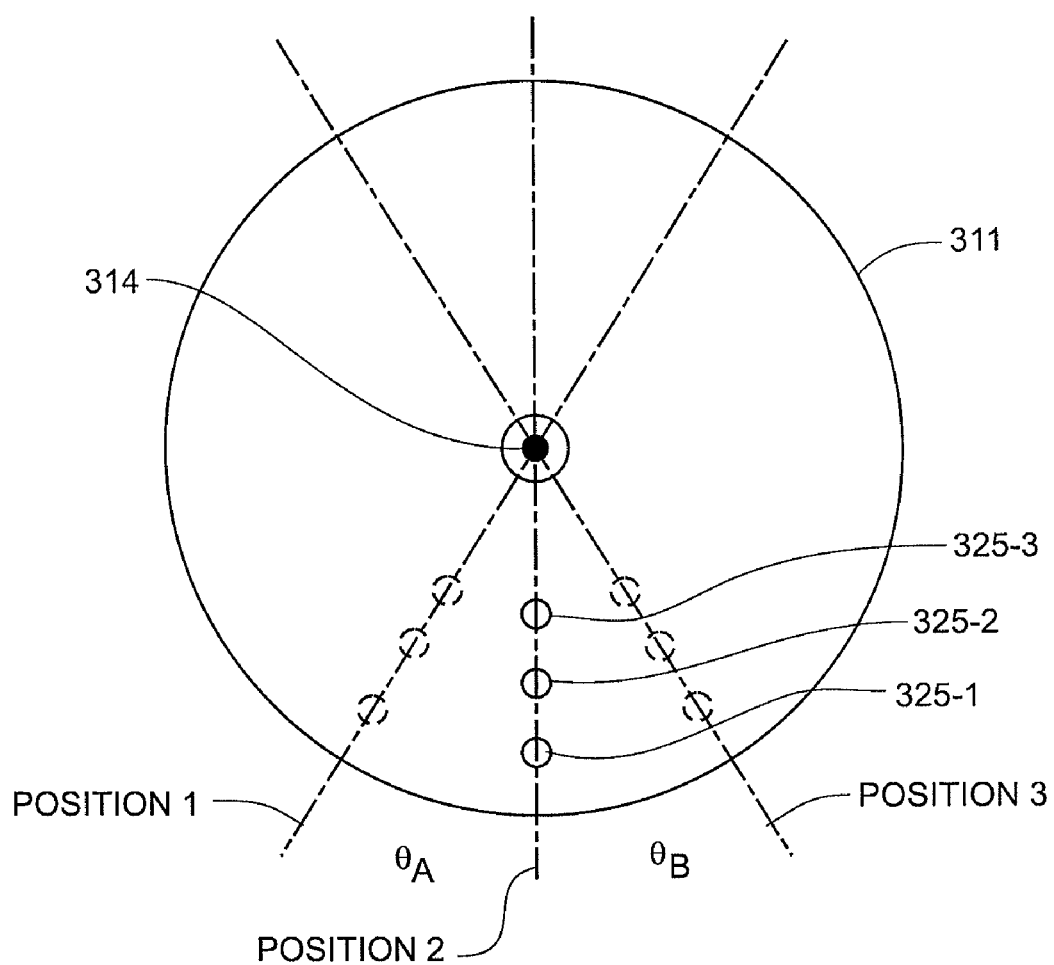

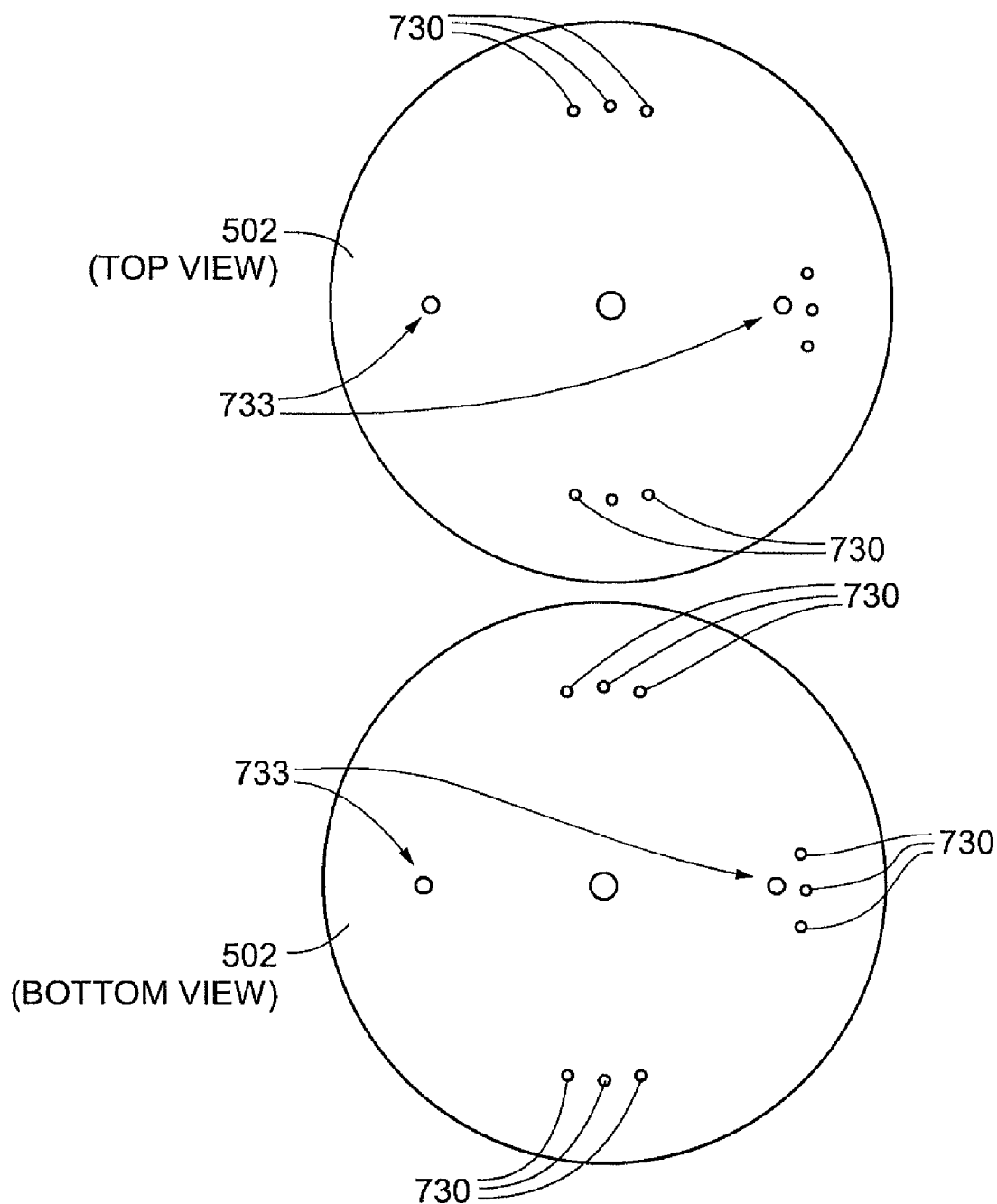

VALVE ANALYTICAL SYSTEM

FIELD

This disclosure generally relates to an analytical system for performing automated wet chemical analysis. In particular, this disclosure relates to a valve analytical system for determining the concentration of a peracid and peroxide within a use composition.

BACKGROUND

An analytical procedure in chemistry consists of a series of operations carried out in fixed sequence which may be considered steps or stages. One step in chemical analytical procedure often involves the delivery of predetermined volumes of one or more fluid chemicals. When performed by hand, analytical chemistry procedures can produce varied results due to a number of factors such as, for example, the usage of an improper or inaccurate volume of a fluid chemical. Moreover, manual analytical chemistry procedures can be tedious and time consuming. Accordingly, there is a desire to automate analytical chemistry procedures.

One application of analytical chemistry is to determine the concentration of one or more analytes within a composition. For example, the analytical chemical procedures can be useful in the analysis and monitoring of antimicrobial compositions. Antimicrobial compositions are used in a variety of automated processing and cleaning applications to reduce microbial or viral populations on hard or soft surfaces or in a body or stream of water. For example, antimicrobial compositions are used in various applications including kitchens, bathrooms, factories, hospitals and dental offices. Antimicrobial compositions are also useful in the cleaning or sanitizing of containers, processing facilities or equipment in the food service or food processing industries, such as cold or hot aseptic packaging. Antimicrobial compositions are also used in many other applications including but not limited to clean-in-place systems (CIP), clean-out-of-place systems (COP), washer-decontaminators, sterilizers, textile laundry machines, filtration systems, etc.

Whatever the application, an antimicrobial or "use" composition is a composition containing a defined minimum concentration of one or more active components which exhibit desired antimicrobial properties. One such category of active antimicrobial component are peracids, such as peroxycarboxylic acid (peracid), peroxyacid, peroxyacetic acid, peracetic acid, peroctanoic acid, peroxyoctanoic acid and others.

The concentration of active components in the use composition is chosen to achieve the requisite level of antimicrobial activity. In use compositions in which one or more peracids are the active component, and in the instance of a recirculating process, the concentration of hydrogen peroxide tends to increase over time while the concentration of peracid decreases. However, in order to maintain the requisite level of antimicrobial activity, the amount of peracid in the use composition must be maintained at a defined minimum concentration. In addition, as the amount of hydrogen peroxide in the use composition increases, the use composition may exceed a defined maximum concentration of hydrogen peroxide in the solution. In some applications, for example bottling line cleansing, the allowable amount of residual hydrogen peroxide is subject to government regulations. Once the hydrogen peroxide concentration exceeds the maximum concentration, the spent use composition is discarded and a new use composition generated.

To ensure that the amount of peracid is maintained at or above some minimum concentration and to determine when the amount of hydrogen peroxide reaches or exceeds a maximum concentration, it is necessary to determine the concentration of peracid(s) and hydrogen peroxide in the use composition. In the past, to determine both the peracid concentration and the hydrogen peroxide concentration in a use composition has required multiple time consuming manual titrations, several different reagents and relatively large volumes of use composition. Moreover, past devices and methods for determining both peracid and hydrogen peroxide concentrations were effective over only a narrow range of concentrations.

SUMMARY

Certain embodiments disclosed herein provide a rotary valve analytical system including a rotor, a stator, syringe and rotor drive motors, a mixer, and an optical sensor. The rotor is rotatable about an axis perpendicular to a face of the rotor and includes a plurality of syringe barrels formed therewithin. The syringe barrels extend into the rotor from openings within the rotor face and are disposed at selected radial distances from the axis. The stator is coaxially positioned relative to the rotor and includes a stator face which opposes and is in sealable, slidable contact with the rotor face. The stator includes a plurality of sets or groups of openings each of which includes a plurality of openings disposed at a common radial distance from the axis which extend through the stator forming passages to an outlet port. The common radial distance of each group of openings is equal to one or more of the selected radial distances of the openings in the rotor face. The syringe drive motor is mechanically coupled with a plurality of plungers and is adapted to drive and withdraw one plunger within each syringe barrel within the rotor. The rotor drive motor is mechanically coupled with the rotor and adapted to cause the rotor to rotate relative to the stator. A plurality of inlet and outlet tubes can be coupled with the outlet ports of the stator to deliver fluid to the system, or deliver dispensed fluid from the system to a device. In some embodiments, the rotary valve analytical system includes a fluid mixer, for mixing delivered fluid and a sensor in fluid communication with the mixer and adapted to perform a measurement on the mixed fluids.

In another aspect, embodiments of the invention include a method for analyzing one or more characteristics of a use composition. The method includes providing a rotary valve analytical system such as, for example, that described above. The method further includes rotating the rotor to a first position, such that the syringe barrels within the rotor are aligned with one or more of the inlet passages within the stator. Additionally in this position, the other openings within the stator face are sealed by the rotor face. One or more of the aligned inlet passages are in fluid communication with the source of the use composition. The method further includes simultaneously drawing fluid into each of the syringe barrels from the aligned inlet passages. Then, the rotor can be rotated to a second position, such that each of the syringe barrels are aligned with one of the outlet passages and the other openings within the stator face are sealed by the rotor face. The fluid within the syringe barrels can then be simultaneously driven through the aligned fluid outlet passages and into outlet lines. In some embodiments, the method further includes mixing the dispensed fluids in the mixer resulting in a sample mixture within the outlet line. Then, one or more properties of the sample mixture can be measured with the sensor. The measured properties may be indicative one or more characteristics of the use composition, which can then be determined based on the measurement.

In another aspect, the invention includes a lab on a valve analytical system for determining a concentration of a peracid and a peroxide within a use composition. The lab on a valve assembly includes a valve assembly, a mixer, and a sensor. The valve assembly includes a rotor, a stator and a plurality of syringe plungers. The rotor has a rotor face and a plurality of syringe barrels extending into the rotor from openings in the rotor face. The rotor is rotatable about an axis perpendicular to the rotor face. The stator is disposed coaxially with the rotor and includes a stator face in sealable, slidable, rotary contact with the rotor face. The stator further includes a plurality of groups of passages, each group of passages including a plurality of passages which extend through the stator from an opening on the stator face to a connector port. Each passage of the groups of passages is disposed at a common radial distance from the axis such that each group of passages can be aligned with at least one syringe barrel of the rotor by rotating the rotor relative to the stator. One of the syringe plungers is disposed within each of the syringe barrels, such that each syringe plunger can draw fluid into and drive fluid from the syringe barrel in which it is disposed. In addition, one or more of the connector ports is in fluid communication with a source of the use composition, one or more of the connector ports is in fluid communication with a source of a reagent, and one or more of the connector ports is in fluid communication with a source of an acid. The mixer is in fluid communication with the connector port of one of the passages of each group of passages of the stator. The mixer is adapted to produce a sample mixture comprising quantities of the use composition, the reagent, and the acid. And, the sensor is in fluid communication with the mixer. The sensor is adapted to measure one or more properties of the sample mixture indicative of the concentration of the peracid and the concentration of the peroxide within the use composition.

These and various other features and advantages will be apparent from a reading of the following detailed description.

BRIEF DESCRIPTION OF THE DRAWINGS

The following drawings are illustrative of particular embodiments of the invention and therefore do not limit the scope of the invention. The drawings are not to scale (unless so stated) and are intended for use in conjunction with the explanations in the following detailed description. Embodiments of the invention will hereinafter be described in conjunction with the appended drawings, wherein like numerals denote like elements.

FIG. 3A is a top plan view of a sample preparation assembly according to some embodiments.

FIG. 3B is a plan view of a rotor of the sample preparation assembly of FIG. 3A.

FIG. 7C shows top and bottom views of the valve disk shown in FIG. 7A.

DETAILED DESCRIPTION OF ILLUSTRATIVE EMBODIMENTS

Figure 1:
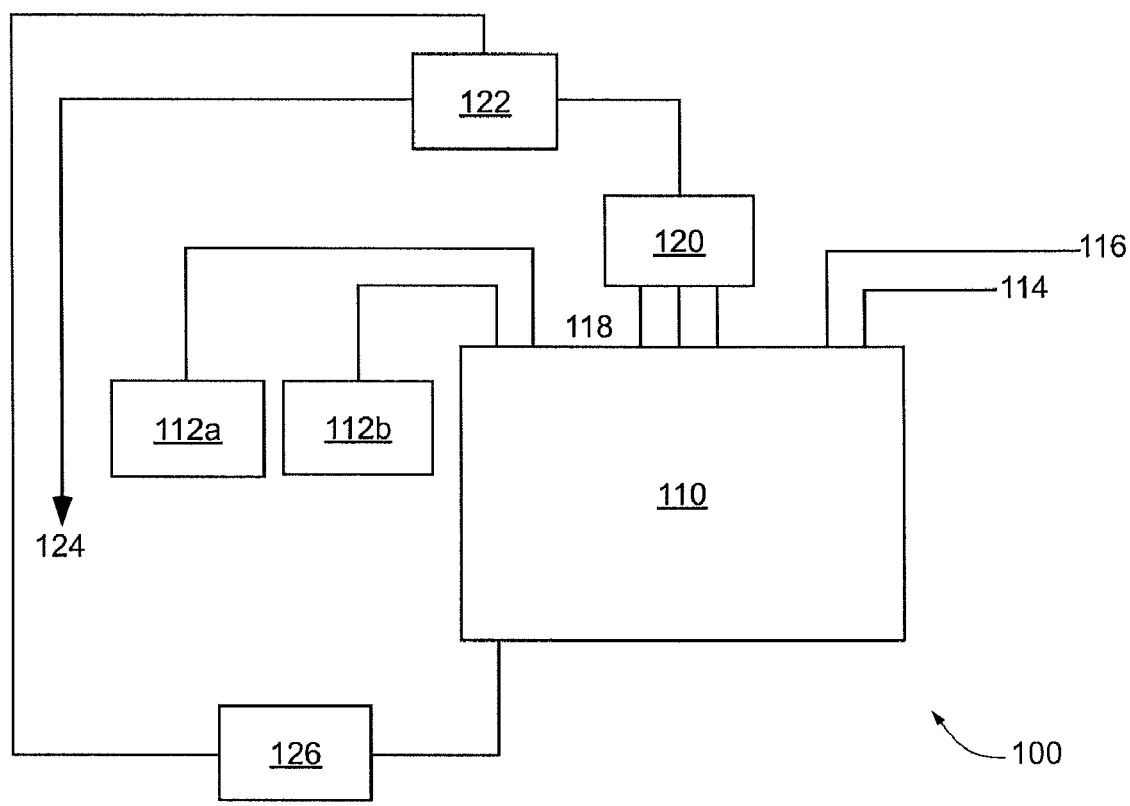
FIG. 1 is a schematic view of a lab on a valve analytical system according to some embodiments.

FIG. 1 shows a schematic view of a lab on a valve analytical system 100 according to some embodiments. The lab on a valve analytical system 100 comprises a sample preparation assembly 110 in fluid connection with sources of fluid inputs 112, 114, 116. The sample preparation assembly 110 manages the simultaneous dispensing of predetermined volumes of selected ones of the connected fluids. The metered fluids are dispensed via fluid outlets 118 connected with the sample preparation assembly 110. A mixer 120 connected with the fluid outlets 118 mixes the dispensed fluids, providing a sample mixture. The sample mixture is delivered to a sensor 122, which can obtain response data indicative of characteristics of the sample mixture. Once the fluid has passed through sensor 122, it can be disposed of via connection to waste 124. Operation of the sample preparation assembly 110 and sensor 122 can be controlled by a controller 126. In addition, the controller can process the response data to determine properties of one or more of the fluids.

Lab on a valve analytical systems, according to some embodiments, enable the automation of manual wet chemical analytical procedures. For example, the lab on a valve system 100 can be configured as a use composition monitor. A use composition monitor may be connected to a source of use composition 114, to monitor characteristics of the use composition such as, for example, the presence or concentration of selected analytes. In particular, some embodiments are well suited for use as a use composition monitor for determining the concentration of peracid and/or hydrogen peroxide in a use composition. For example, the use composition may be monitored to ensure that the concentration of peracid satisfies at least a minimum threshold concentration. The use composition may also be monitored to determine when the concentration of hydrogen peroxide exceeds a maximum threshold concentration. Of course, embodiments of the lab on a valve analytical systems disclosed herein should not be limited to monitoring devices, for example, such systems can be used as analytical instruments or for other purposes.

In some embodiments, the lab on a valve analytical system 100 can be adapted to perform a kinetic assay procedure for determining the concentrations of peracid and/or hydrogen peroxide in the use composition. This is accomplished by exploiting the difference in reaction rates between peracid and hydrogen peroxide when using, for example, a buffered iodide reagent to differentiate peracid and hydrogen peroxide concentrations when both these analyte compounds are present in the use composition. In such use the inputs of the sample preparation assembly 110 can be coupled with a source of reagent 112a, a source of an acid 112b, and a source of the use composition 114. In addition, some embodiments can include a connection to a source of water 116. The use composition monitor may also determine the concentrations of peracid and/or hydrogen peroxide in the presence of other additional ingredients, such as acidulants, one or more stabilizing agents, nonionic surfactants, semi-polar nonionic surfactants, anionic surfactants, amphoteric or ampholytic surfactants, adjuvants, solvents, additional antimicrobial agents or other ingredients which may be present in the use composition.

In a use composition including hydrogen peroxide and a peracid such as peroxyacetic acid, a buffered iodide changes color as it is oxidized by both the peroxyacetic acid and the hydrogen peroxide to form triiodide ion. However, as the peroxyacetic acid and the hydrogen peroxide in the use composition compete for the available iodide ions, reaction with the peroxyacetic acid proceeds at a faster rate than the reaction with the hydrogen peroxide, as shown in the following equations:

$$2CH_3COOOH + (excess)I^- \rightarrow I_3^- + 2CH_3COOH \quad \text{FASTER}$$

$$H_2O_2 + (excess)I^- + 2H^+ \rightarrow I_3^- + 2H_2O \quad \text{SLOWER}$$

This difference in reaction rates may be exploited to differentiate peracid and hydrogen peroxide concentrations when both these analyte compounds are present in the use composition. For example, an optical sensor 122 can measure colorimetric data as a function of time of a sample within the sensor 122. This data can include, for example, absorbance data of a sample mixture undergoing the above reactions. Because the triiodide product of the above reactions manifests as a change in absorbance, the measured colorimetric data can be used to determine the concentrations of peracid and peroxide within the use composition. In particular, the initial absorbance, $A_0$, is dependent on the peracid concentration and independent of the peroxide concentration; and the rate of change in absorbance, $A_t$, is dependent on the concentration of peroxide and independent of the peracid concentration. Accordingly, measurements of the initial absorbance $A_0$ and the rate of change of absorbance $A_t$ can be utilized to determine values of peracid and peroxide concentration within a use composition. This calculation is described in more detail in commonly owned U.S. patent application Ser. No. 12/370,369, entitled, "Wide Range Kinetic Determination of Peracid and/or Peroxide Concentrations," which is hereby incorporated by reference.

The concentrations of peracid and/or peroxide determined by the lab on a valve use composition monitor 100 may be used, for example, as feedback to another system to maintain the peracid concentration in the use composition within a predefined range. If, for example, the concentration of peracid in the use composition decreases below a predetermined level, the use composition may be replenished by adding a concentrated peracid composition to the use composition. As another example, if the concentration of peroxide in the use composition exceeds a predetermined level, the use composition may be replenished by emptying the use composition vessel of the spent use composition and generating a new use composition.

Figure 2A:
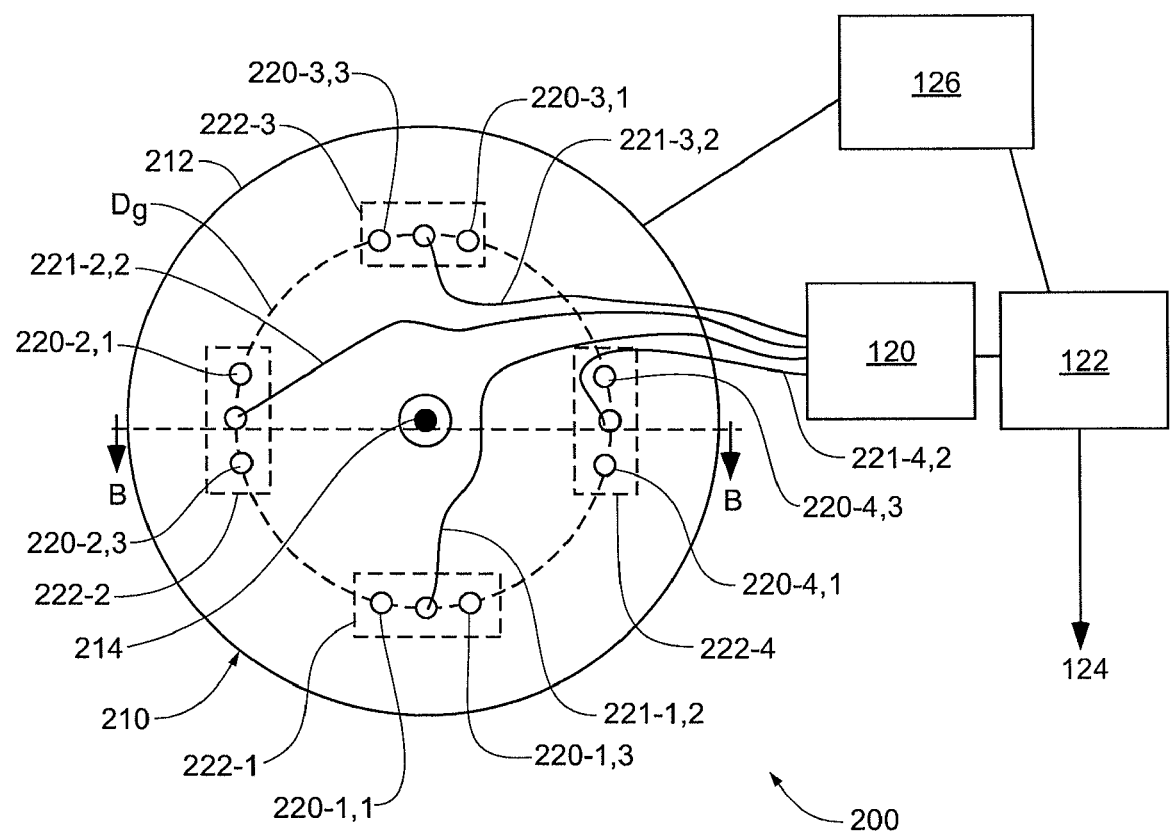
FIG. 2A is a top plan view of a sample preparation assembly according to some embodiments.

FIG. 2A shows a top plan view of a lab on a valve analytical system 200 according to some embodiments. The lab on a valve analytical system 200 comprises a rotary valve analytical system comprising a sample preparation assembly 210 having a plurality of fluid inputs and fluid outputs. The fluid outputs of the sample preparation assembly are connected with a mixer 120 which is connected with a sensor 122 and a waste line 124. As above, the system 200 can be controlled by a controller 126. The sample preparation assembly 210 provides for the synchronous delivery of a plurality of fluids to the mixer 120 and sensor 122. Thus, sample preparation can be processed in parallel, rather than the serial preparation of sample mixtures characteristic of sequential injection analysis systems. Parallel processing of sample mixtures can afford significant reductions in sample preparation time, thus decreasing the time required to perform a measurement cycle. Accordingly, embodiments according to the present invention can provide for more frequent use composition analysis. For example, in some embodiments, analytical systems adapted to determine the concentrations of peracid and peroxide within a use composition can perform a measurement in approximately 5 seconds.

Figure 2B:
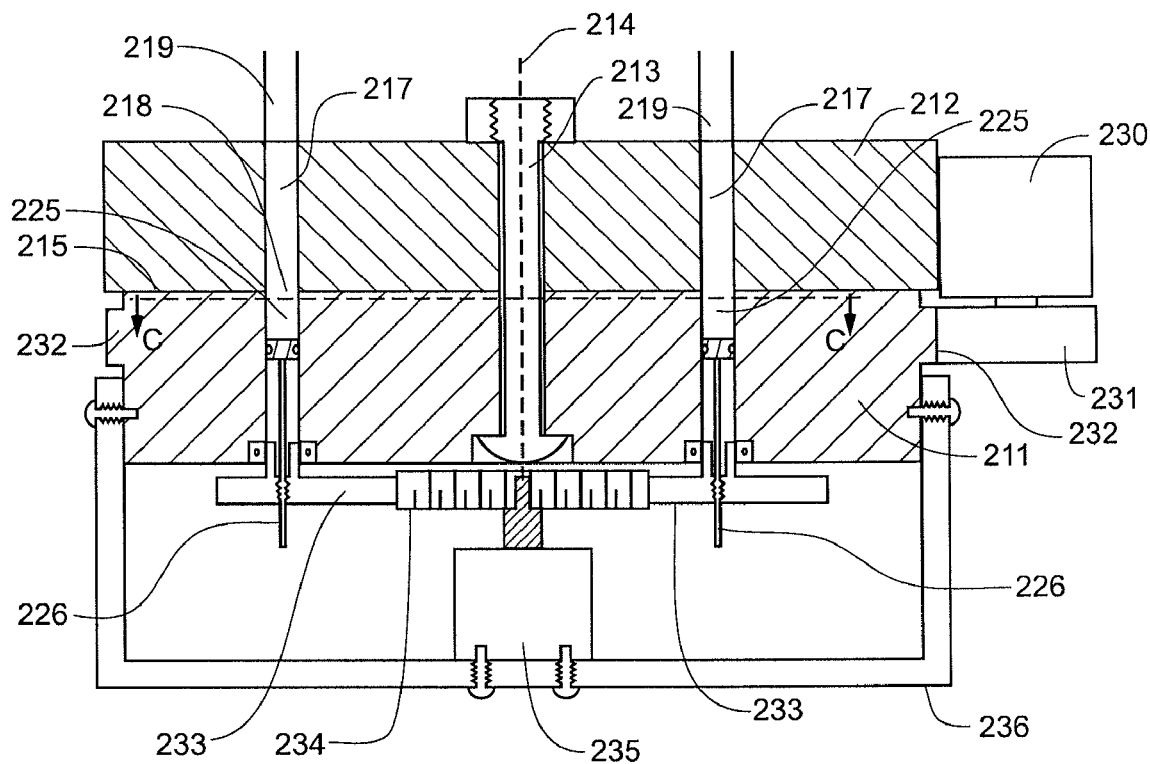
FIG. 2B is a cross-sectional view of the sample preparation assembly of FIG. 2A from the perspective of lines B-B.
Figure 2C:
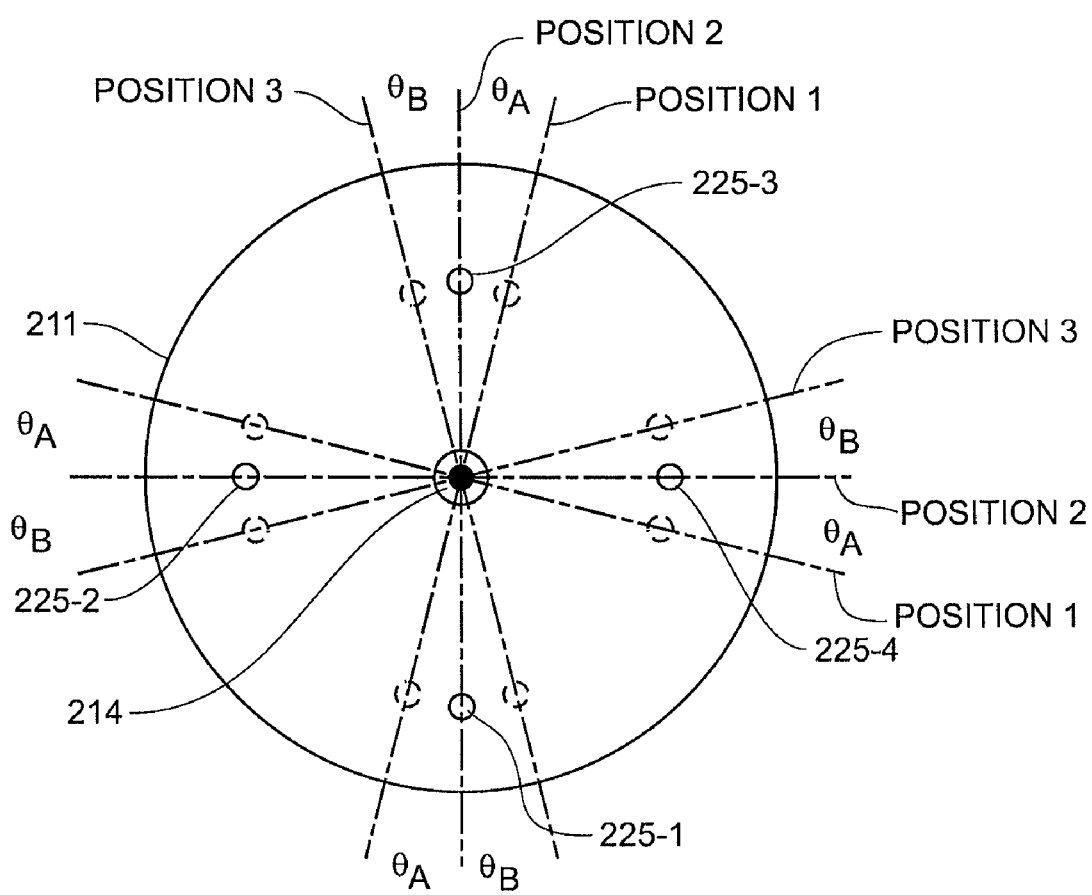
FIG. 2C is a plan view of a rotor of the sample preparation assembly of FIG. 2B from the perspective of lines C-C.

The sample preparation assembly 210 will be described with reference to FIGS. 2A, 2B, and 2C. FIG. 2A shows a top plan view of a sample preparation assembly 210 according to some embodiments. FIG. 2B shows a cross-sectional view of the sample preparation assembly 210 of FIG. 2A from the perspective of lines B-B. FIG. 2C shows a plan view of a rotor 211 of the sample preparation assembly of FIG. 2B from the perspective of lines C-C.

With reference to FIG. 2B, the sample preparation assembly 210 comprises a rotor 211 rotatably mounted to a stator 212. The rotor 211 and stator 212 are coupled by a bolt 213 which defines an axis of rotation 214 about which the rotor 211 is rotatable. The bolt 213 provides a compression force, holding a face of the rotor 211 in sealable, slidable contact with a face of the stator 212 at an interface 215. The rotor stator face and rotor face interact such that the rotor face can slide over the stator face as the rotor 211 rotates about the axis 214 while maintaining a fluid seal such that fluid cannot seep between the two faces at the interface 215.

The stator 212 further comprises a plurality passages 217 passing therethrough. The passages 217 extend through the stator from openings 218 at the stator face to outlet ports 219. The outlet ports 219 can be connected with fluid inlet connectors 220 or outlet connectors 221 as shown in FIG. 2A. The passages 217 within the stator 212 are arranged into groups of passages 222. Any reference made herein to a passage by a single part number shall be construed as referring to all passages within the sample preparation assembly. Individual passages will be referred to by the group and passage number of the passage to which it connects. For example, passage 217-1,1 is the first passage of the first group of passages 222-1. Likewise, passage 217-3,2 is the second passage of the third group of passages 222-3. In addition, any reference herein to inlet connectors and/or outlet connectors by a single part number shall be construed as referring to all inlet connectors or outlet connectors coupled with the sample preparation assembly. References to individual inlet connectors or individual outlet connectors will be made by including the group and passage number to which the connector connects. For example, inlet connector 220-1,1 is the inlet connector connected to passage 217-1,1 and outlet connector 221-3,2 is the outlet connector connected to passage 217-3,2.

For example, the embodiment of FIG. 2A shows a stator 212 having four groups of passages 222. Each group of passages 222 comprises three passages. Each of the passages of a selected group of passages is disposed at a common radial distance from the axis 214. For example, each of the passages of group 222-1 of the embodiment of FIG. 2A are disposed a radial distance $D_g$ from the axis 214. Moreover, in some embodiments, common angular distances separate the passages within each of the groups of passages. For example, the angular distance separating passage 217-1,1 and passage 217-1,2 is equivalent to the angular distance separating (i) passages 217-2,1 and 217-2,2, (ii) passages 217-3,1 and 217-3,2, and (iii) passages 217-4,1 and 217-4,2.

Referring to FIG. 2B, the sample preparation assembly 210 further comprises a rotor 211. The rotor 211 is rotatable relative to the stator 212. The rotor 211 includes a plurality of syringe barrels 225 formed therein. Each syringe barrel 225 extends into the rotor 211 from an opening on the rotor face. The syringe barrels 225 are disposed within the rotor at selected radial distances $D_s$ from the axis 214 such that one syringe barrel is associated with each of the groups of passages 222 within the stator 212. That is, the selected radial distance $D_s$ of at least one syringe barrel 225 is equal to the common radial distance $D_g$ for each group of passages. Accordingly, when the rotor 211 is rotated such that an opening on the rotor face aligns with an opening on the stator face, the passage 217 connects the syringe barrel 225 with the connected inlet or outlet connector.

FIG. 2C shows a top plan view of a rotor 211 according to some embodiments. From this view, the rotor face and plurality of openings, which form syringe barrels 225 therein, are visible. This embodiment includes four syringe barrels 225. Each syringe barrel is positioned relative to the axis such that it corresponds with a single group of passages 222 within the stator. For example, syringe barrel 225-1 is positioned at a selected radial distance $D_s$ that is equivalent to radial distance $D_g$ of group 222-1, such that syringe barrel 225-1 is associated with group 222-1 of FIG. 2A. Moreover, the additional syringe barrels of the rotor are positioned relative to syringe barrel 225-1 such that alignment of syringe barrel 225-1 with a passage of group 222-1, will cause each of the other syringe barrels within the rotor to align with the corresponding passage of a different group of passages. For example, in FIG. 2C, the rotor is shown rotated such that syringe barrel 225-1 is in position 2. In this position, the syringe barrel 225-1 is aligned with passage 217-1,2 of the stator (i.e. a connection is made between the syringe barrel 225-1 and outlet connector 221-1). In addition, this rotor position 2 further aligns (i) syringe barrel 225-2 with passage 217-2,2, (ii) syringe barrel 225-3 with passage 217-3,2, and (iii) syringe barrel 225-4 with passage 217-4,2.

In operation, rotor 211 can be rotated to change the alignment of syringe barrels and passages. In embodiments where the passages 217 in each group of passages 222 are separated by common angular distances, rotation of the rotor can be used to select which of the passages 217 are connected with the syringe barrels 225. For example, rotation of the rotor 211 of FIG. 2C by an angle $\theta_A$, i.e. to position 1, will result in aligning syringe barrel 225-1 with passage 217-1,1 of the stator 212. Likewise, syringe barrel 225-2 will be aligned with passage 217-2,1, syringe barrel 225-3 will be aligned with passage 217-3,1, and syringe barrel 225-4 will be aligned with passage 217-4,1. Similarly, rotation of the rotor 211 by an angle $\theta_B$ transitions the rotor to position 3, thus aligning each of the syringe barrels 225 with the third passage 217-x,3 of each group of passages 222-x.

Rotation of the rotor 211 can be accomplished, for example, by the actuation of a rotor drive motor 230. The rotor drive motor 230 can be coupled with the stator 212 and adapted to drive a rotor drive gear 231. Rotor teeth 232 disposed along the perimeter of rotor 211 can engage rotor drive gear 231 such that as rotor drive gear 231 is driven, rotor 211 rotates about axis 214. One of ordinary skill will appreciate other ways to drive rotor 211, all of which should be considered within the scope of invention.

Each syringe barrel 255 is adapted to receive a plunger 226. Each plunger 226 comprises a drive shaft and a plunger head. The plunger head is disposed within the syringe barrel 225 so as to form a fluid-tight seal with the walls of the syringe barrel 225. This seal may be facilitated, for example, by the inclusion of a rubber o-ring positioned about the perimeter of the plunger head. The plunger drive shaft is coupled with the plunger head and adapted to position the plunger head within the syringe barrel 225. For example, in some embodiments, the plunger drive shaft comprises a threaded shaft threadably engaged with a syringe gear 233 at the end opposite the plunger head. Rotation of the syringe gear 233 causes the shaft (and thus the plunger head) to translationally shift within the syringe barrel 225. Moreover, the plunger can include a means for preventing rotation of the plunger drive shafts. This can be, for example, a pin through the plunger drive shaft which is received within a corresponding slit in the body of the rotor 211. Such an arrangement allows the shaft and pin to move translationally during rotation of the syringe gear 233. Another way to eliminate the possibility of rotation plunger is to offset the plunger drive shaft from the center of the plunger head. Alternatively, in some embodiment the plunger heads and syringe barrels can be oval in shape to prevent rotation of the plunger head. Accordingly, the syringe barrels 225 and plungers 226 act as syringe pumps, where fluid can be drawn into the syringe barrel via the opening in the rotor face by withdrawing the plunger head and fluid can be delivered from the syringe barrel via the opening the rotor face by driving the plunger into the syringe barrel.

In some embodiments, two or more of the syringe pumps can be simultaneously controlled. For example, a syringe drive gear 234 driven by a syringe drive motor 235 can contact each of the syringe gears 233. Activation of the syringe drive motor 235 can drive the syringe drive gear 234, which in turn drives each of the connected syringe gears 233. In some embodiments, the syringe drive motor 235 can be coupled with a housing 236 that encloses the rotor so as to protect the mechanical components from physical interruption. Of course, other syringe pump drive schemes can be applied, for example, each syringe pump can include its own drive motor such that each of the plungers are separately controllable. Moreover, the threadable connection to each drive shaft can be selected such that a single drive motor can be used to drive multiple plungers for different distances. Each of these and other variations that are within the capabilities of one of ordinary skill in the art should be considered within the scope of invention.

Thus, the rotor is provided with a plurality of pumps. Each of the pumps is embedded within the rotor such that an opening in the rotor face provides the inlet to the pump. The pumps are configured to selectively draw in fluid from an aligned passage, hold the fluid, and drive the fluid out of the pump to an aligned passage. In many embodiments, the rotor is rotated as fluid is held within the pump, thus the passage to which fluid is driven is not the same passage from which the fluid was drawn. Thus, the pumps, combined with the rotation of the rotor, can effectuate delivery of fluid from an inlet passage to an outlet passage. While the embodiments described herein have referenced syringe pumps, generally any micropump capable of accomplishing the above described function can be utilized. For example membrane micropump with thermal, electrostatic, or piezoelectric actuation can be used.

Thus, embodiments of the sample preparation assembly 210, can provide for simultaneous delivery of multiple fluids to one or more fluid outlets 221. For example, the rotor 211 can be rotated to position 1, such that the syringe barrels 225 of the rotor are aligned with the first stator passages 217-x,1. At this position, the syringe barrels are in fluid communication with the first passages, and thereby the fluid sources connected to the first passages 217-x,1 via inlet connectors 220-x,1. The other openings within the stator face abut the rotor face and are thereby sealed shut. Fluid can be drawn into each of the syringe barrels by simultaneously activating the syringe pumps, for example, by drawing the plungers 226 within the syringe barrels 225.

Once a desired volume of fluid has been drawn into the syringe barrel 225, the rotor can be rotated to second position 2. At position 2, each of the syringe barrels 225 are aligned with one of the passages 217-x,2 connected with an outlet connector 221. During rotation, fluid remains sealed within the syringe barrel by the sealed connection of the opening within the rotor with the stator face. Moreover, the additional passages within the stator are sealed by the opposing rotor face, thus preventing leakage of fluid from passages connected with inlet connectors 220. Upon reaching position 2, the fluid can be simultaneously driven from the syringe barrel 225, for example, by simultaneously driving the plungers 226 into the syringe barrels 225. Thus a plurality of fluids can be simultaneously delivered from the sample preparation assembly 210.

In some embodiments the fluid inlet connectors 220 comprise tubes. Likewise, the outlet connectors 221 can comprise tubes. Connections to the sample preparation assembly can comprise generally any fluid-tight connection. For example, the tubes can comprise standard 1 mm diameter tubing connected to the sample preparation assembly via threaded ferrule connection. Suitable tubing and connectors are available, for example, from Valco Instruments Co. Inc., of Houston, Tex. Alternatively, in some embodiments, the inlet and or outlet passages can comprise internal passages formed within sample preparation assembly. One example is shown with respect to FIGS. 5A-7D discussed below, where the passages are formed by sealed channels etched into a portion of an interface disk.

FIGS. 3A and 3B show views of an alternative embodiment of a sample preparation assembly according to some embodiments. FIG. 3A is a top plan view of the sample preparation assembly 300. FIG. 3B is a plan view of a rotor 311 of the sample preparation assembly 300 of FIG. 3A. This embodiment is similar to that shown in FIGS. 2A-2C, however here, each group of passages 322 of the stator 312 is arranged at a distinct common radial distance $D_g$-1, $D_g$-2, $D_g$-3 from the axis 314. Accordingly each inlet connector 320 and outlet connector 321 is radially aligned about the stator 312 such that simultaneously actuated inlet connectors (i.e. inlet connectors 320-x,1 or inlet connectors 320-x,3) and outlet connectors 321-x,2. Likewise, with reference to FIG. 3B, the rotor 311 includes a plurality (here three) of syringe barrels 325 formed therein. These syringe barrels 325 are aligned at radial distances from the axis 314 such that one syringe barrel corresponds with each of the groups of passages 322 within the stator 312. Accordingly, for example, syringe barrel 325-1 is associated with the passages of group 322-1, etc. In operation, rotation of the rotor 311 to position 1, causes the syringe barrels to align with each of the passages 320-x,1. This position can correspond to a measurement cycle, for example, with passage 320-1,1 connected with a source of sample, passage 320-2,1 connected with a source of reagent, and passage 320-3,1 connected with a source of acid. Likewise, the passages 320-x,3 along position 3 can correspond with a reagent blank cycle as described above.

Referring back to the lab on a valve system 100 of FIG. 1, some embodiments further comprise a mixer 120. The mixer 120 can be coupled with the sample preparation assembly 110 via mixer line outlets 118. For example, in the embodiment of FIG. 2A, the mixer line outlets comprise the outlet connectors 221. The outlet connectors 221 provide for simultaneous delivery of multiple fluids to the mixer 221. Upon reaching the mixer 120, the fluids from each of the mixer line inputs are mixed.

The mixer 120 can provide thorough mixing of metered fluid volumes dispensed by the sample preparation assembly 110. In a use composition monitor, appropriate mixing can ensure that the response data measured by the sensor 122 leads to an accurate determination of the characteristic of the use composition to be determined. The mixer 120 may be implemented using any conventional device designed to rapidly mix together two or more fluids. For example, the mixer 120 may be a piece of tubing with internal baffles that cause flow reversal of the fluids to result in rapid mixing. The mixer 120 may also be implemented using a knotted reactor, reaction coil, serpentine or other fluid mixing device known in the art. An example baffle-type static mixer is the Series 120 Individual Mixing Elements available from TAH Industries Inc, Robbinsville, N.J. However, it shall be understood that any suitable mixer may be used without departing from the scope of the present invention, and that the invention is not limited in this respect.

Mixed or otherwise dispensed fluid can then be delivered to a sensor 122. The sensor measures at least one characteristic of the fluid mixture indicative of the properties to be determined. The measurements obtained by sensor 122 are referred to herein as "response data." For example, properties to be determined can be the concentrations of peracid and/or hydrogen peroxide in a use composition. Controller 126 determines the properties based on the response data. In some embodiments, the sensor 122 is an optical detector that measures the transmittance and/or the absorbance of the fluid mixture. In such embodiments, the response data may be the optical transmittance data or optical absorbance data of the sample as a function of time. In other embodiments, the sensor 122 may measure other characteristics indicative of the particular property to be determined, such as fluorescence, pH, oxidation-reduction potential, conductivity, mass spectra and/or combinations thereof. In such embodiments, the response data would be the corresponding measured characteristic at the appropriate points in time. Example sensors 122 include photometric, pH, ORP, conductivity or other sensors. The photometric sensors utilized can operate in the visible, ultraviolet or infrared wavelength range, although other luminescence detection techniques may also be used without departing from the scope of the present invention. One example of a suitable commercially available photometric detector can be assembled using a DT-MINI-2 Deuterium Tungsten Source, FIA-Z-SMA-PEEK Flow Cell and USB4000 Miniature Fiber Optic Spectrometer, all available from Ocean Optics Inc., Dunedin, Fla. It shall be understood, however, that any suitable optical detector may be used without departing from the scope of the present invention, and that the invention is not limited in this respect. Indeed, an appropriate optical sensor may be any of those described for use with respect to U.S. patent application Ser. No. 12/370,369, which is presently co-owned and is herein incorporated by reference.

In the case of an optical sensor, the voltage response of the sensor corresponds to the amount of the light transmitted through the sample mixture. Sensor 122 thus essentially measures the change of the sample solution optical properties within the sensor 122 as a function of time. The transmittance is the ratio of the intensity of light coming out of the sample (I) to intensity of light incident to the sample ($I_0$), $T=I/I_0$. Once the transmittance of the sample is measured, the absorbance (A) of the sample may be calculated. The absorbance or optical density (A) is a logarithmic function of the transmittance; $A=-\log_{10} T=-\log_{10} I/I_0=\log_{10} I_0/I$. With respect to embodiments used to determine the concentrations of peracid and peroxide within a use composition, as is discussed above, the initial absorbance of the sample ($A_0$) is indicative of the concentration of peracid in the use composition and the sample absorbance variation over time is indicative of the concentration of hydrogen peroxide in the use composition. However, as is further indicated, this relationship may not hold true across wide ranging use composition concentrations. For example, at higher concentrations, e.g. above 500 ppm peracid, concentration of peracid is a function of both initial absorbance and, to a lesser degree, absorbance over time. Accordingly, to provide instruments capable of accommodating use with a wide concentration range, i.e. a range encompassing both concentration ranges described above, alternative methods must be utilized.

Additionally, the wavelength tested by the optical sensor can be selected based upon the particular application of the lab on a valve analytical system. Indeed, some embodiments include sensors incorporating emitters of multiple wavelengths. With respect to peracid/peroxide concentration determination, wavelength selection is based on the spectral response of the triiodide complex, and may be within the range of 350 to 450 nanometers, for example. A two wavelength system may utilize the wavelengths 375 nanometers and 405 nanometers, for example.

Some embodiments of lab on a valve analytical systems are optimized for use as an on site use composition monitor. That is, there is a need for accurate and reliable sensors to measure use composition properties, e.g. peracid and peroxide concentrations, when ambient temperature can vary in wide range. Unstable temperature inside of a system has been found to contribute to random variations in concentration readings. Potential causes of such temperature instability include environmental temperature variances and locally generated heat and air flow from components of the measurement system such as pumps, step motors, and electronic components, such as, the controller. Thus, some embodiments include additional features to adjust the temperature of the fluid mixture within the sensor or prior to reaching the sensor. In addition, systems according to some embodiments provide means for adjusting or stabilizing the temperature of sample prior to delivery to the detector to avoid the inconsistencies associated with in field operation. Such systems may include those described in commonly owned U.S. patent application Ser. No. 12/370,369, which has been incorporated by reference herein.

An advantage of lab on a valve systems according to embodiments of the present invention is that they can be set up to automate multiple measurement sequences. For example, the lab on a valve analytical system 200 of FIG. 2A can be set up to carry out two distinct measurement sequences. For example, one sequence, "the sample measurement sequence," can be utilized to measure the concentration of peracid/peroxide within a use composition. The second sequence, "the reagent blank sequence," can be utilized to calibrate the system such that response data collected during the measurement sequence corresponds only to the use composition. The two measurement sequences will be described below.

In the sample measurement sequence use composition, reagent, and acid are connected to a common inlet connector of each of the groups 222 of the sample preparation assembly 210. For example, each of these components can be connected with the first inlet connector 220-x,1 of each group 222. In particular, inlet connector 220-1,1 can be connected with a source of the use composition, inlet connector 220-2,1 can be connected with a source of reagent, and inlet connector 220-3,1 can be connected with a source of acid. Inlet connector 220-4,1 may be coupled with a source of diluent, or alternatively in some embodiments, it may not be used. If one inlet or outlet connector in a group is not used then all connectors of this group should be not used and not plugged because the plugged connector will restrict movement of the plunger associated with this group of connectors. As described above, with respect to the determination of concentration of peracid/peroxide within a use composition, the reagent can comprise potassium iodide, and the acid can comprise acetic acid.

Continuing with the sample measurement sequence, the sample preparation assembly 210 can manage the simultaneous delivery of volumes of the components. This can be accomplished as described above. In the sample measurement sequence, the result is that metered volumes of use composition, reagent, and acid are delivered via the outlet connections 221. These fluids are directed to the mixer 120 which thoroughly mixes the fluids and provides a sample mixture. The sample mixture is delivered to the sensor 122, where response data is collected. Following the collection of response data, the sample mixture can be disposed of along waste line 124. A controller 126, can then process the response data to determine the concentrations of peracid and/or peroxide within the use composition.

The reagent blank sequence manages the preparation and testing of a "reagent blank" to determine calibration data that can be used in calculating the final output, e.g. peracid/peroxide concentration, during the measurement sequence. The reagent blank comprises a volume of mixed fluids equal in volume to that which will be tested during the measurement sequence, but with a fluid having a known absorbance replacing the use composition. For example, the reagent blank can comprise water, reagent, and acid, the water having a known absorbance.

For the reagent blank sequence, water, reagent, and acid can be connected to a common inlet connector of each of the groups 222 of the sample preparation assembly 210. For example, each of these components can be connected with the third inlet connector 220-x,3 of each group. In particular, inlet connector 220-1,3 can be connected with a source of water, inlet connector 220-2,3 can be connected with a source of reagent, and inlet connector 220-3,3 can be connected with a source of acid. Inlet connector 220-4,3 may be coupled with a source of diluent, or alternatively in some embodiments, it may not be used.

Continuing with the reagent blank sequence, the sample preparation assembly 210 can manage the simultaneous delivery of volumes of the components as described above. However, here, rather than rotating to position 1, the rotor is rotated to position 3, to provide connection with the components of the reagent blank. The result is that metered volumes of water, reagent, and acid are delivered via the outlet connections 221. These fluids are directed to the mixer 120 which thoroughly mixes the fluids and provides the reagent blank. The reagent blank is delivered to the sensor 122, where response data is collected. Following the collection of response data, the reagent blank can be disposed of through a connected waste line 124. A controller 126, can then process the response data to determine offsets or other calibration values to be utilized in the measurement sequence calculations. These offsets may be due to contributions to absorbance of the reagent or acid itself, or other environmental considerations. Thus, embodiments according to the present invention can manage the preparation and analysis of multiple samples, i.e. a measurement sample and a reagent blank sample. One of ordinary skill in the art will recognize that other sample preparations (e.g. samples utilizing additional sample sources, different reagents, etc.) may be substituted for, or added in addition to the reagent blank sequence described above.

Some embodiments comprise a measurement unit that combines all essential components for sample preparation and measurement in one analyzer unit. Such a unit can be used to manage all steps of the analytical operation, from sample preparation to measurement calculation and output. In some embodiments, the measurement unit can be a portable measurement unit.

Figure 4A:
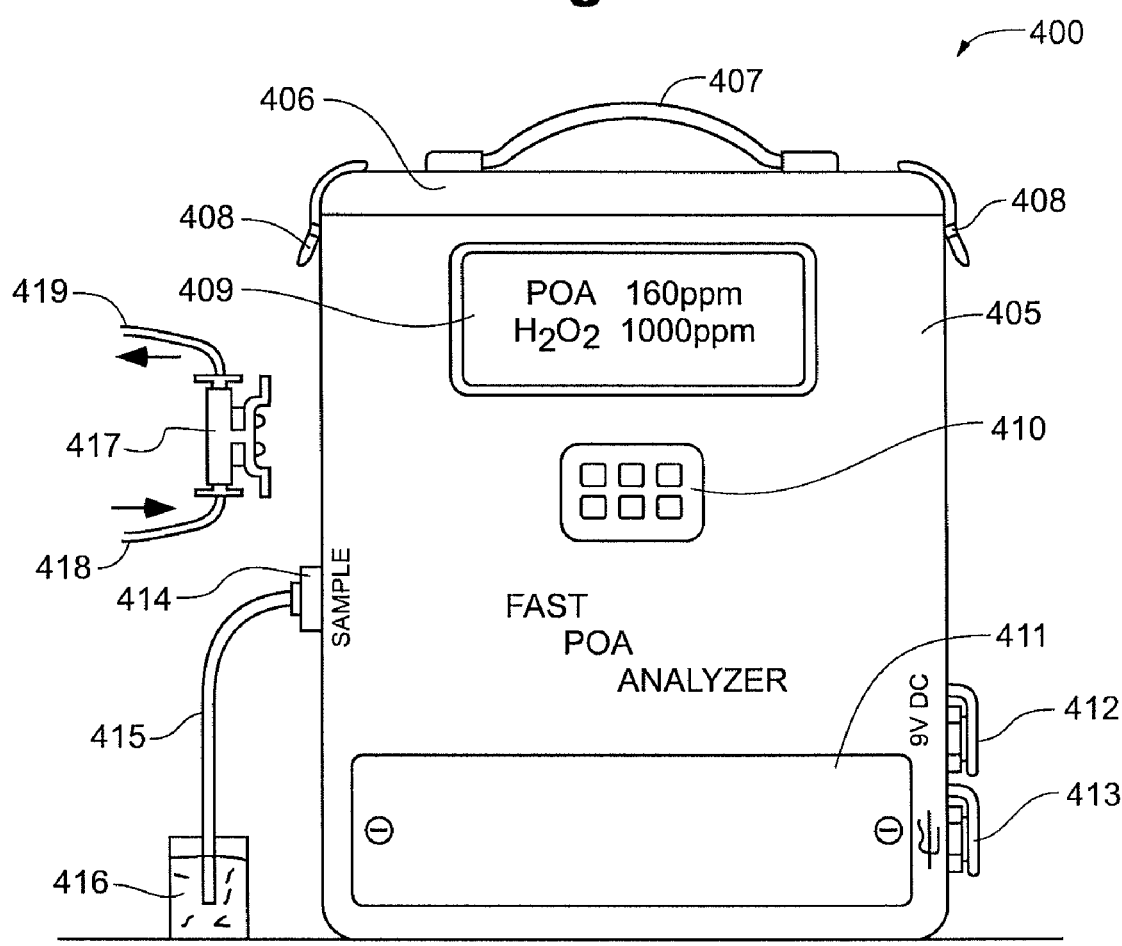
FIG. 4A is a front view of a portable analyzer according to some embodiments.
Figure 4B:
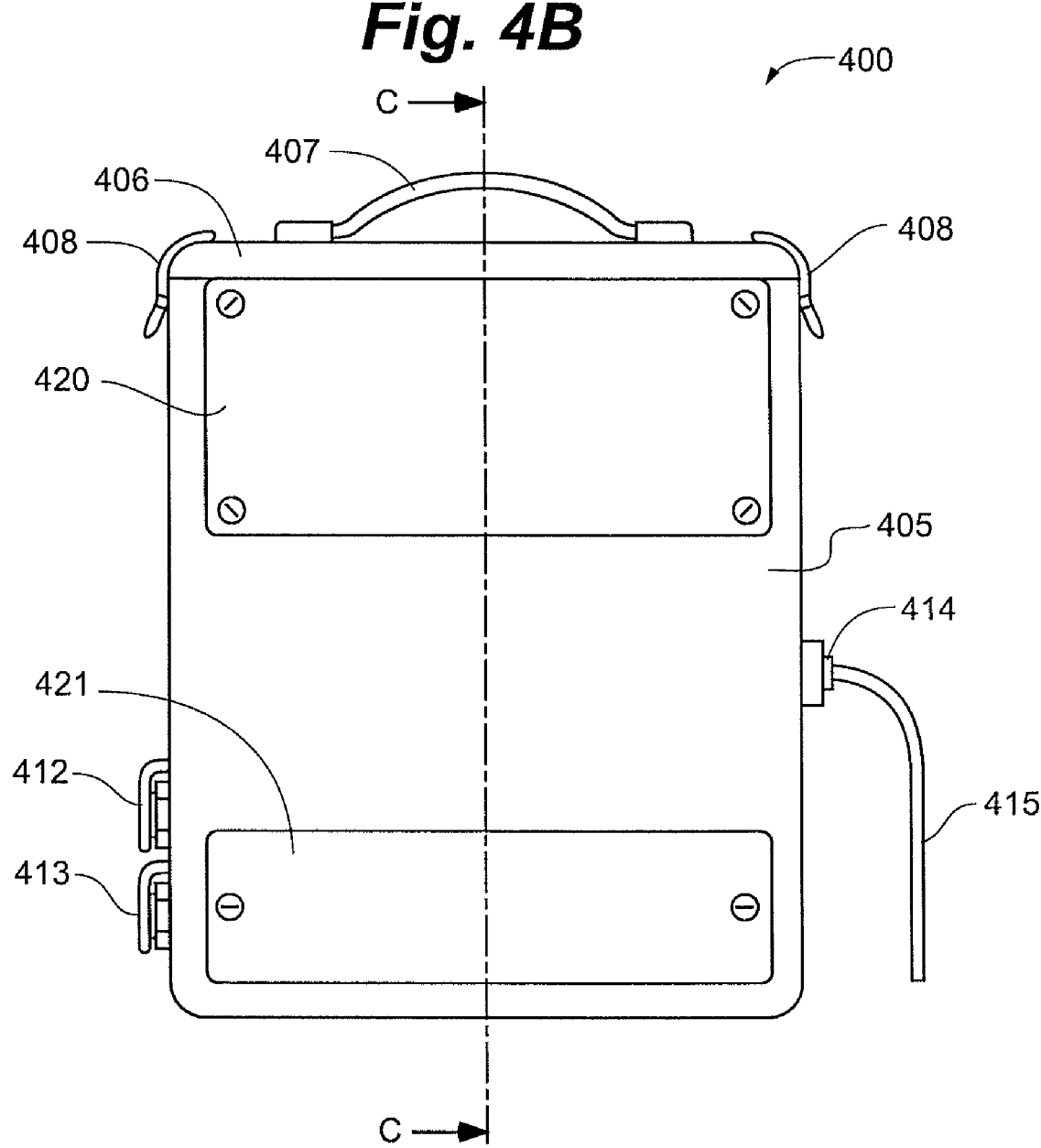
FIG. 4B is a rear view of the portable analyzer of FIG. 4A.

For example, FIGS. 4A and 4B show front and rear views, respectively, of a portable analyzer 400 according to some embodiments. The portable analyzer 400 includes a splash-proof housing 405, which houses the analytical device components. The splash-proof housing 405 has a lid 406 with a handle 407 secured by locks 408. The front wall of the analyzer 400 includes a display 409, keypad 410, and battery compartment cover 411. According to some embodiments, the analyzer 400 is powered by a 9 V power source. Such power can be supplied by battery (e.g. nine AA batteries) or from a 9V DC power supply via a DC power connector 412. In addition, the analyzer 400 can include a USB or other connection port 413 which can provide for connection to a computer or monitoring system via USB or other appropriate cable.

Additionally, the analyzer 400 includes one or more connections to a sample source. The sample source connection can comprise an input port 414 having a polyfluorocarbon input tube 415 (for example 0.50 mm ID, 10 cm length PTFE tubing TTF-120 from VICI Valco Instruments Co. Inc., Houston, Tex.). The input tube 415 can be used during calibration, or for analyzing a discrete sample 416. For continuous monitoring, a sampling flow cell 417 can be connected directly to the sample input port 414. By this arrangement, use composition continuously flows from an input tube 418 into an output tubing 419 of the sampling flow cell 417, providing fresh solution for analysis.

FIG. 4B shows a rear plan view of the analyzer 400 of FIG. 4A. At the rear, the analyzer 400 can include an input access cover 420 and a waste access cover 421.

Figure 4C:
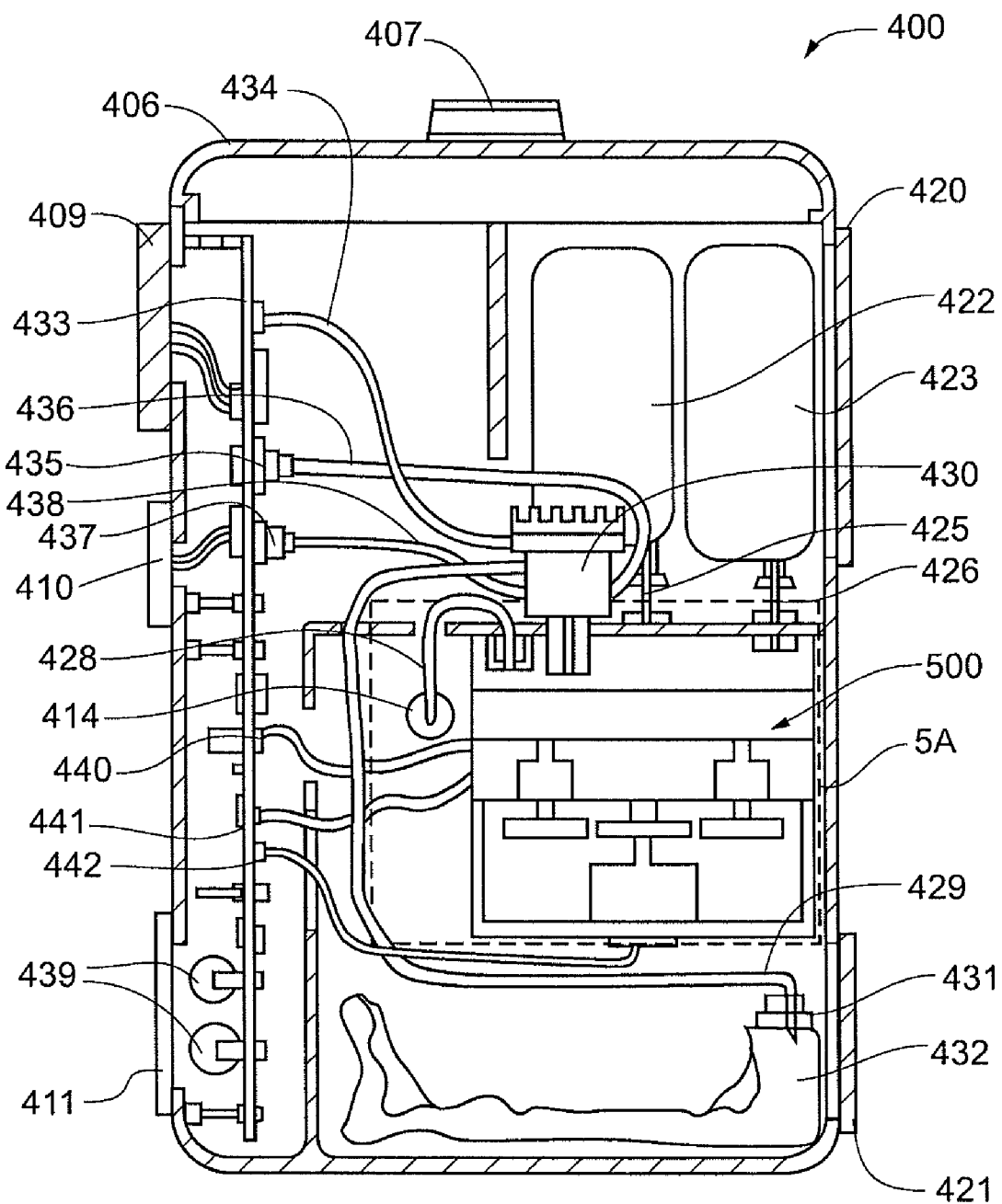
FIG. 4C is a cross-section view of the analyzer of FIG. 4B from the perspective of lines C-C.

FIG. 4C shows a cross-section of the analyzer 400 along the plane C-C. With the locks 408 open, the lid 406 can be removed to provide access to replaceable solution reservoirs located within the housing 405. In addition, the input access cover 420 can be removed to provide easy access to such reservoirs. The replaceable solution reservoirs provide sources of solutions, or components utilized during the wet chemical analytical procedures performed by the device. For example, with respect to a peracid/peroxide analyzer, the solution reservoirs can comprise a KI reservoir 422, an acid reservoir 423, and a water reservoir (not visible in this view). In some embodiments, the replaceable solution reservoirs can comprise metalized plastic bags having a puncturable interface. The puncturable interface of each bag can be directly connected to a corresponding needle port of the lab on a valve assembly 500 which is contained within the analyzer 400. Each of the bags has volume approximately 200 ml which stays in degassed condition during operation. Solution bags of this volume can provide for approximately 3000 analysis sequences, at which time, the reservoirs should be replaced or refilled. Each of the needle port connections can have internal volumes less than 10 µl and create a sealed connection to the water and reagents providing for extended reagent lifetime, e.g. at least 6 months.

Needle ports 425, 426 (and others if necessary) provide for input connection from solution reservoirs to the lab on a valve assembly. Sample input connection can be provided by a short polyfluorocarbon tubing 428 (for example 0.50 mm ID, 10 cm length PTFE tubing TTF-120 from VICI Valco Instruments Co. Inc., Houston, Tex.) connected from input port 414 to the lab on a valve assembly 500. Additionally, waste tubing 429 can provide fluid output from the lab on a valve assembly 500. The waste tubing 429 can extend through optical cell 430 and include a needle connector 431 at its end, allowing for a sealed connection to a waste bag 432 through a puncturable interface. The waste bag 432 can have a volume of approximately 800 ml. During use, the waste bag can be emptied or replaced when new water and reagent bag reservoirs are installed in the analyzer 400. The waste bag 432 can be replaced by removing access cover 421 in the housing 405 of the analyzer 400. Alternatively, the waste tubing 429 can connect with an external output connector which can allow waste solution to continuously flow out of the housing 405.

The analyzer 400 further includes an electronics board 433 which contains all electronic device controls, electronic drivers, and power supplies. The electronics board 433 can be secured vertically within the housing 405, adjacent the internal surface of the front panel to allow access to the electronic components mounted therein. The electronics board 433 can include, for example, a controller, memory, and real time clock, for carrying out the various measurement sequences associated with the analyzer 400 and performing the calculations necessary to determine the desired unknown. For example, the controller can be used to determine the concentrations of peracid and peroxide within a use composition based upon response data collected from an optical sensor. Accordingly, the electronics board 433 can include various sensor and control connectors. For example, the electronics board 433 can include a light emitting diode in a mount 435 in optical communication with a first optical fiber 436, and a photodiode in a mount 437 in optical communication with a second optical fiber 438. The first optical fiber 436 can be used to deliver light to the optical cell and the second optical fiber 438 can collect the delivered light after it has passed through a volume of the sample. Readings from the photodiode 437 can thus comprise the response data. In addition, the electronics board 433 can comprise other components for calibrating or monitoring the optical cell such as, for example, a connection 434 to a temperature sensor located at the optical cell. The control outputs of the electronics board 433 can include an electrical driver 440 for controlling a thermoelectrical cooler coupled with the optical cell. This electrical driver 440 can comprise a single input driver which is based off of input from the temperature sensor 434, such as the temperature control circuit described in commonly owned U.S. patent application Ser. No. 12/370,362, entitled "H-Bridge Control Circuit," which is hereby incorporated by reference. Moreover, the electronics board 433 can include first and second electrical drivers 441, 442 for controlling the electrical step motors used to control the lab on a valve assembly 500.

Additionally, the electronics board 433 can include I/O connectors. For example, the electronics board 433 can include a connection for outputting data to the display 409, a connection for communicating with the keypad 410, and/or a connection for communicating with the USB or other connection port 413. In some embodiments, power supply components can be integrated with the electronics board 433. For example, the electronics board can include connection to an external power supply and/or holders for batteries 439.

Figure 5A:
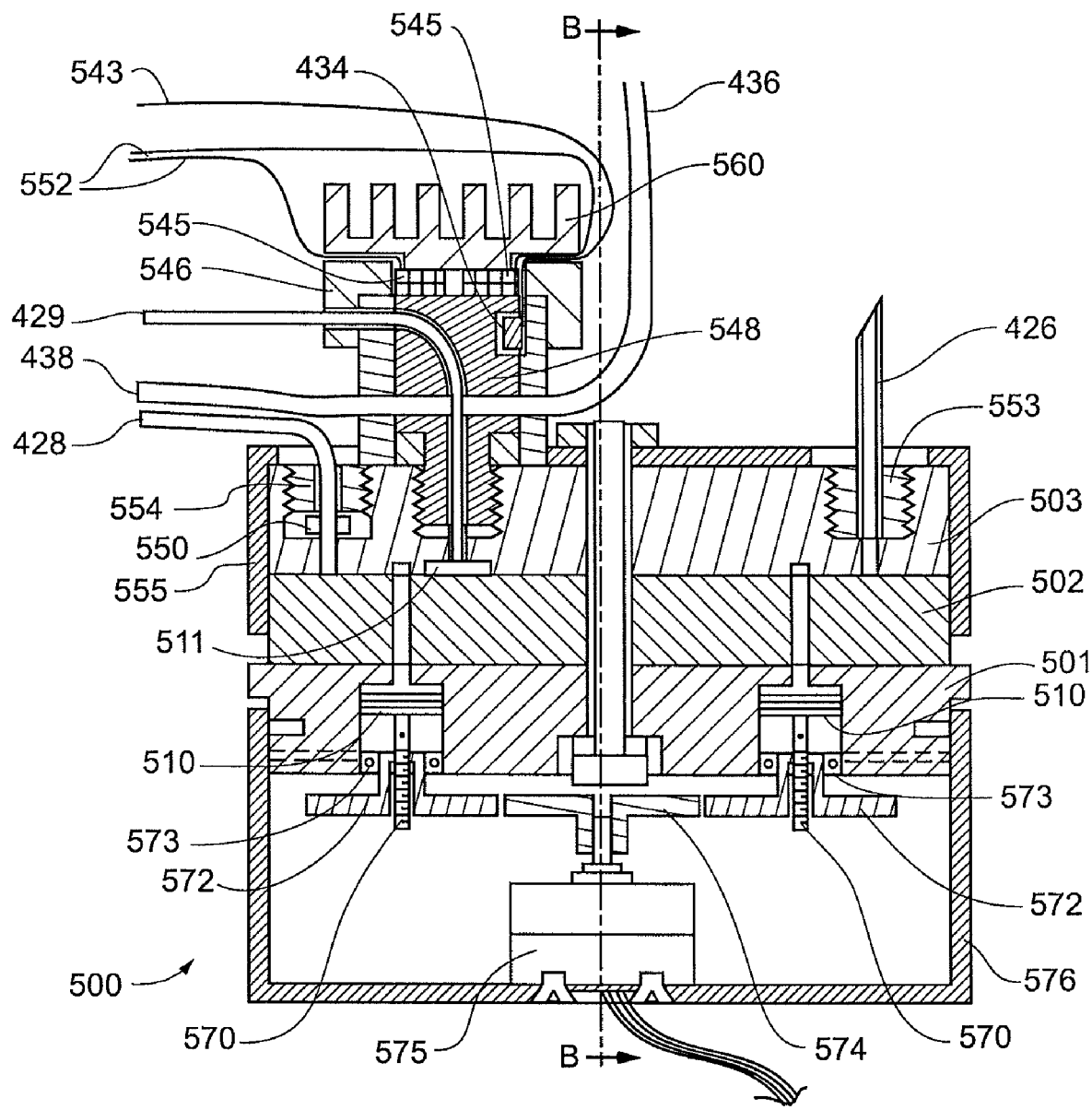
FIG. 5A is a cross-sectional view of the lab on a valve assembly indicated by region 5A of FIG. 4C.
Figure 5B:
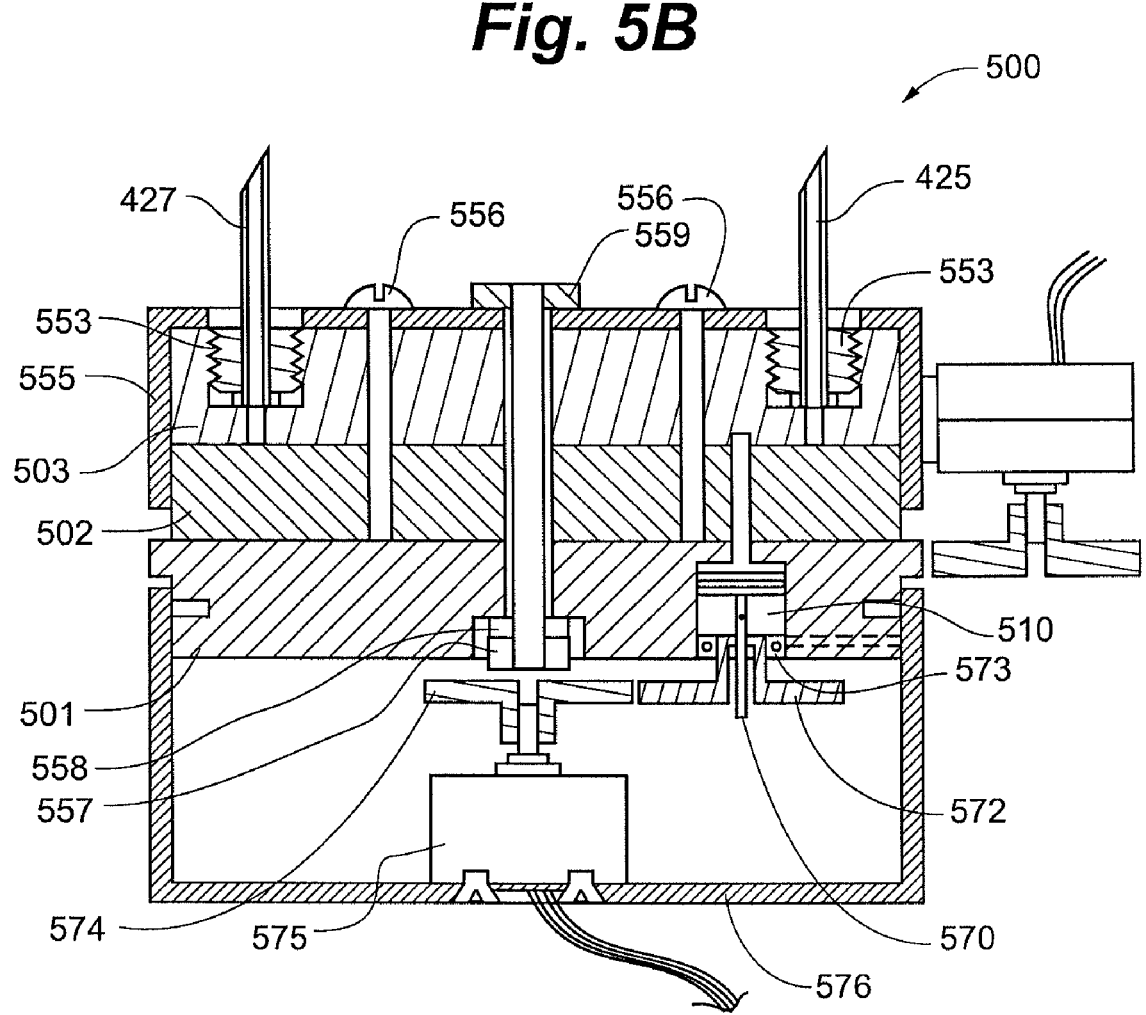
FIG. 5B shows a cross-sectional view of the lab on a valve assembly of FIG. 5A along the plane B-B.
Figure 6A:
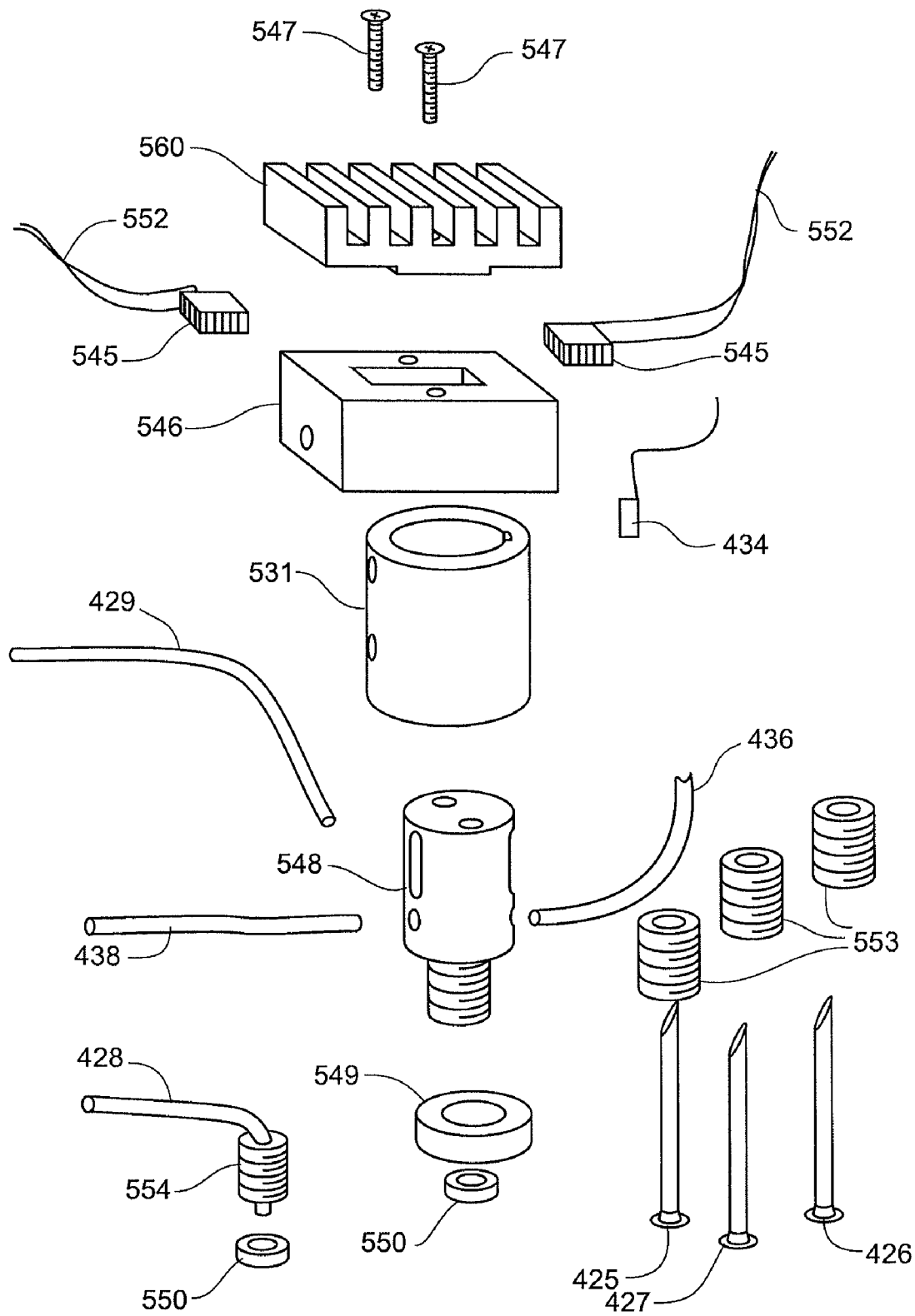
FIGS. 6A-6C show an exploded view of the lab on a valve assembly of FIGS. 5A and 5B.
Figure 6B:
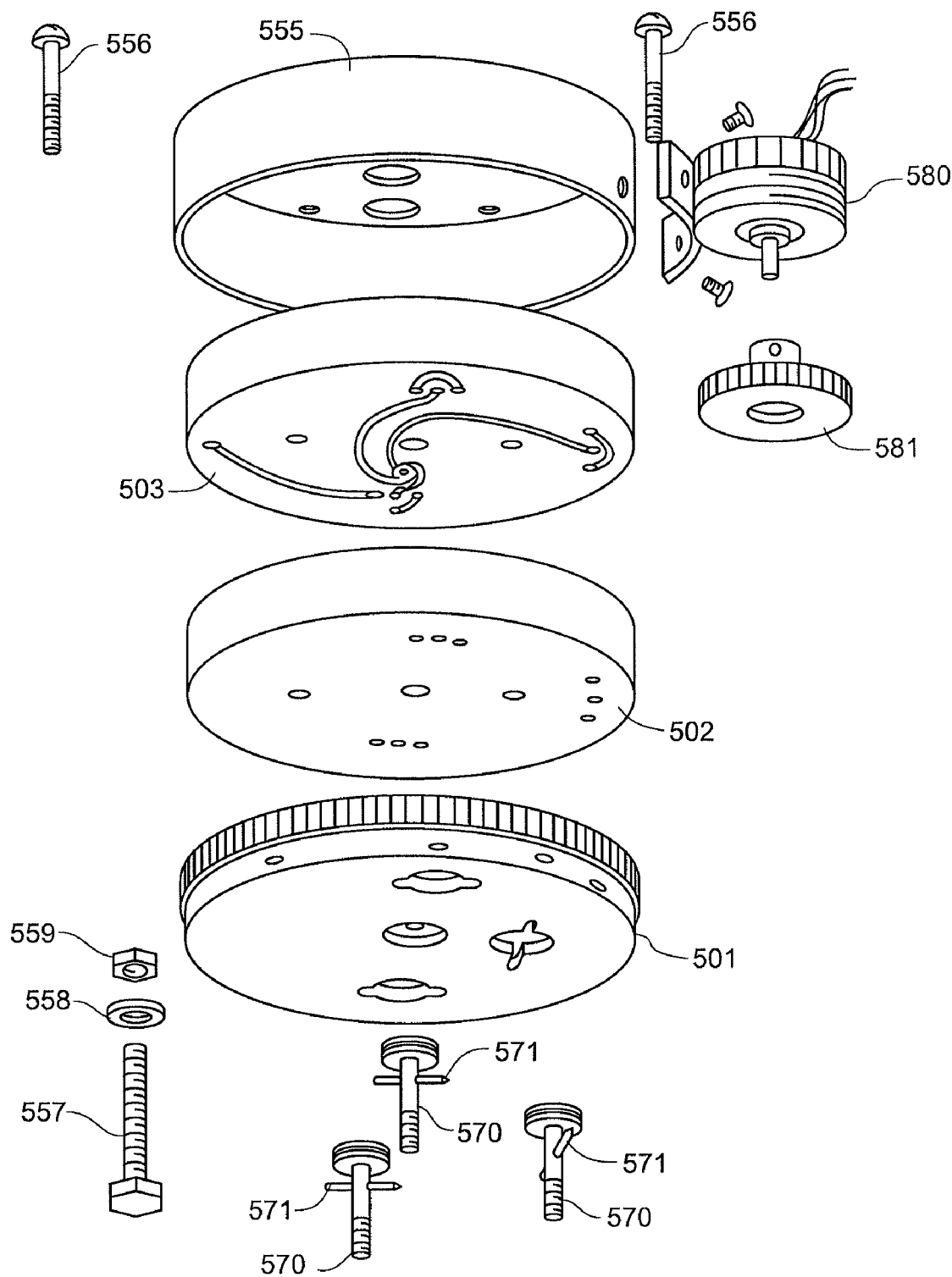
Figure 6C:
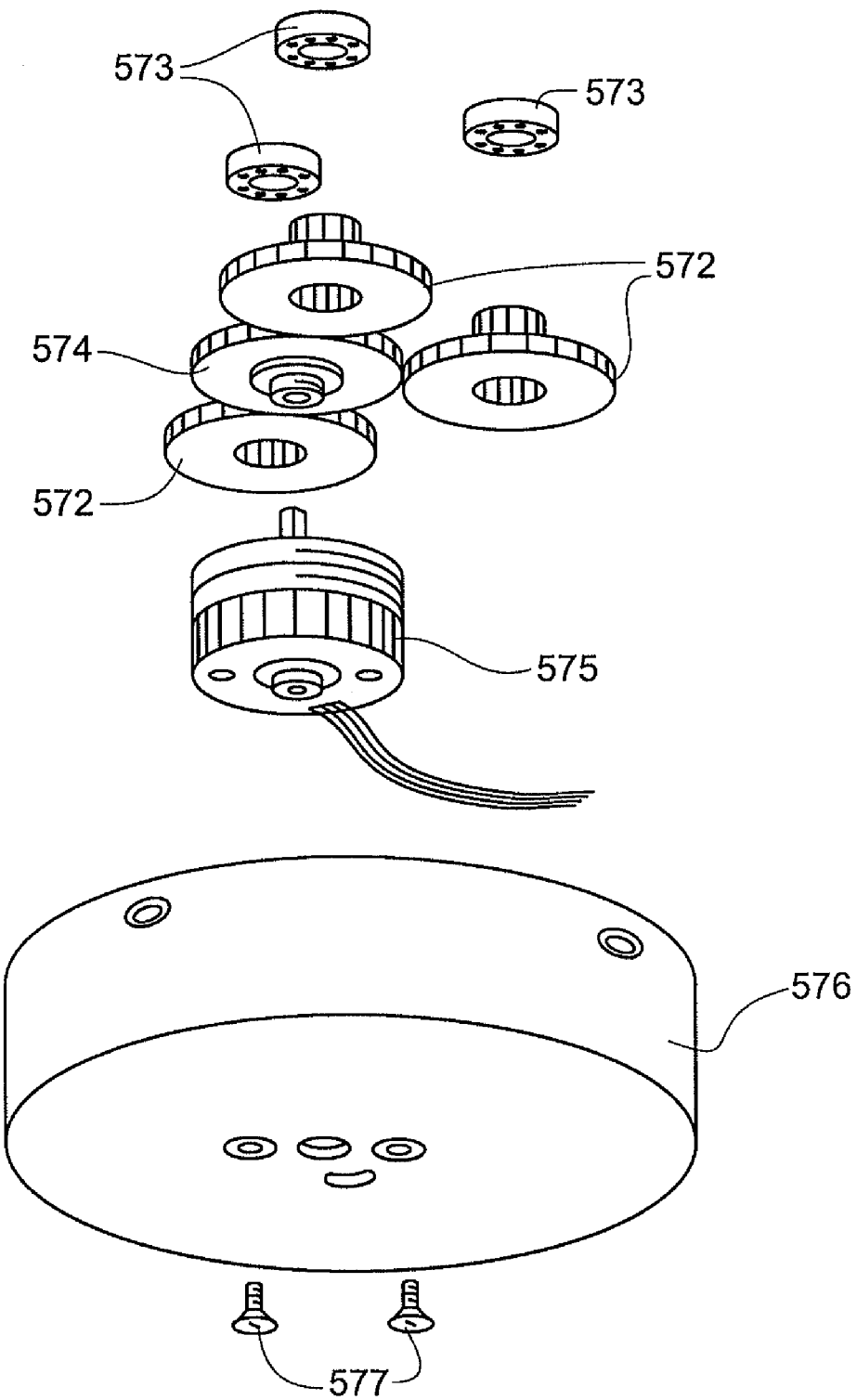
Figure 7A:
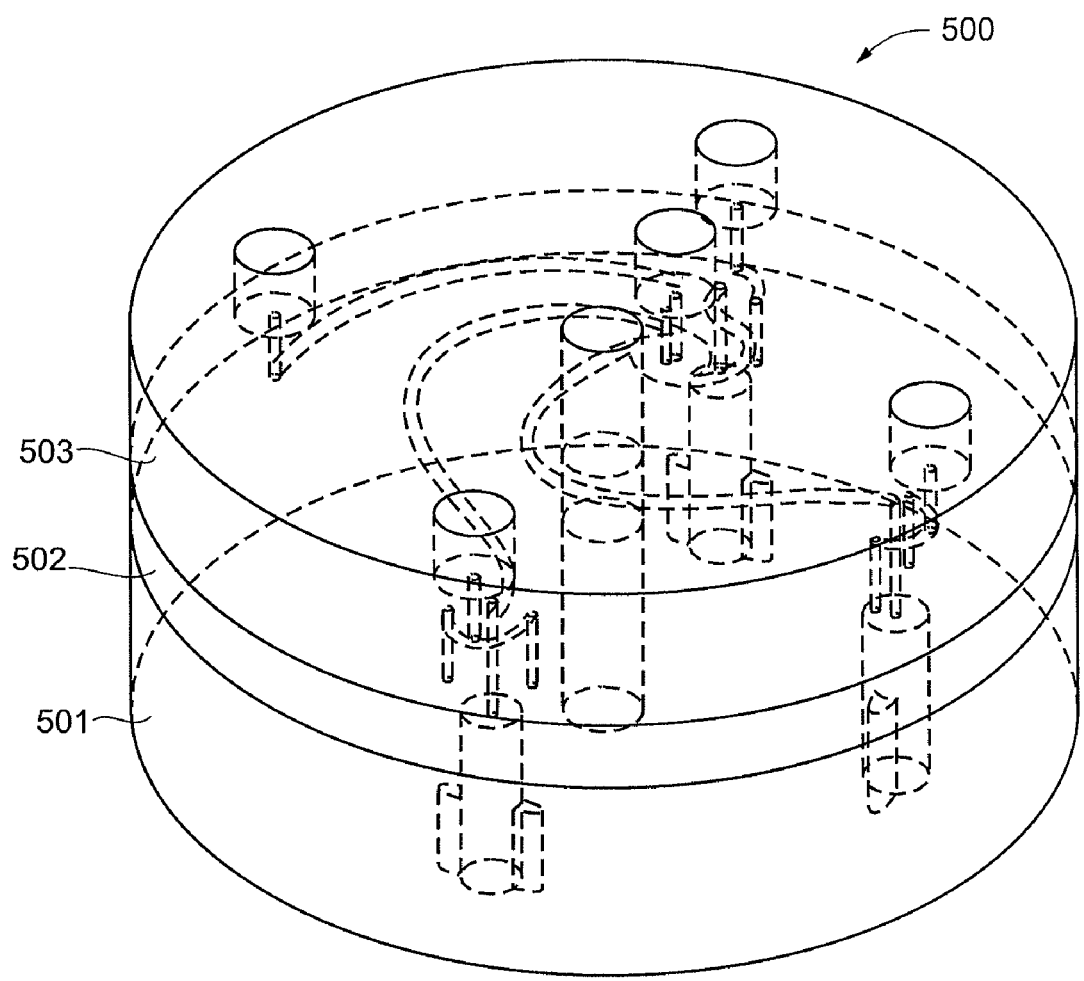
FIG. 7A shows a transparent, perspective view of the disks which comprise a lab on a valve assembly according to some embodiments.
Figure 7B:
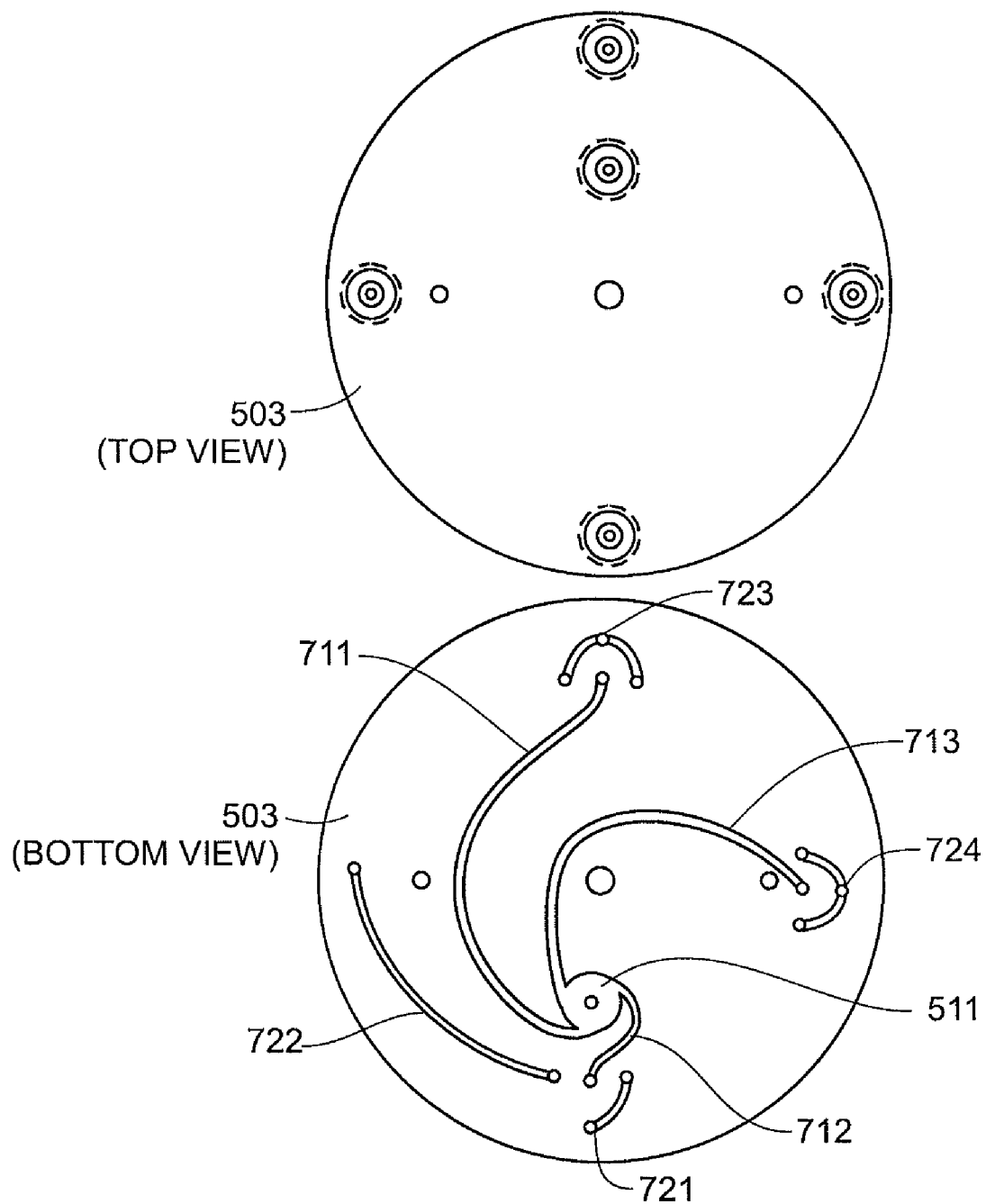
FIG. 7B shows top and bottom views of the interface disk shown in FIG. 7A.
Figure 7D:
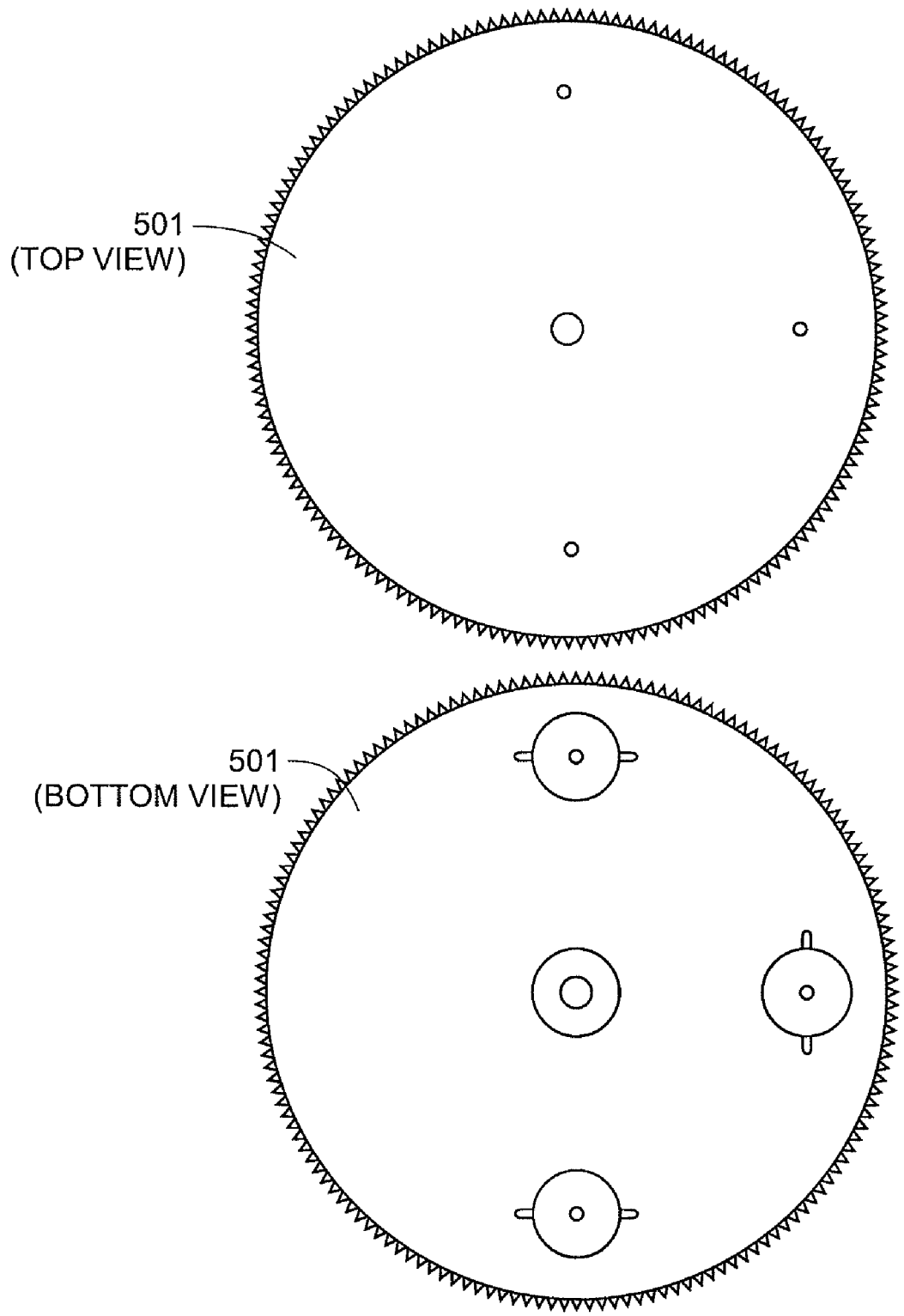
FIG. 7D shows top and bottom views of the rotor disk shown in FIG. 7A.

The lab on a valve assembly 500 of the portable analyzer 400 is shown in greater detail in FIGS. 5A and 5B. FIG. 5A shows a cross-sectional view of the lab on a valve assembly 500 as indicated by region 5A of FIG. 4C. FIG. 5B shows a cross-sectional view of the lab on a valve assembly 500 along the plane B-B of FIG. 5A. FIGS. 6A-6C show an exploded view of the lab on a valve assembly 500. FIG. 7A shows a transparent, perspective view of the disks which comprise the lab on a valve assembly. Additionally, FIGS. 7B-7D show top and bottom views of the three disks 101, 102, 103 shown in FIG. 7A. FIG. 7B shows top and bottom views of the interface disk 103. FIG. 7C shows top and bottom views of the valve disk 102. FIG. 7D shows top and bottom views of the rotor disk 101. While it includes an additional layer not disclosed in the lab on a valve assemblies described above, the principles and general operation associated with the particular embodiment of the lab on a valve assembly disclosed in FIGS. 5A-7D is commensurate with the embodiments described above with respect to FIGS. 2A-3B. Accordingly, the variations and features of the lab on a valve assemblies described above can be incorporated into the embodiments shown in FIGS. 5A-7D. In addition, nothing disclosed herein is intended to limit the use of a particular lab on a valve assembly with the analyzer 400 or other devices disclosed herein.

The lab on a valve assembly 500 of FIGS. 5A-7D comprises three stacked disks 501, 502, 503 which can be seen in FIG. 5A. The rotor disk 501 comprises internal micro pumps 510 and can be rotated around the vertical axis to be set in several discrete positions relative to the valve disk 502. The valve disk 502 is fused or clamped to an interface disk 503 which includes connection ports for receiving sample input tubing 528, reagent bags (via needle connectors 425, 426, 427), and the sensor assembly. In some embodiments, the interface disk 503 further includes an integral mixer 511 (this integral mixer can take the place of an external mixer as shown in FIG. 1). The interface disk 503 and the valve disk 502 can be secured within a valve cover 555 by screws 556. These screws 556 can engage the disks 503, 502 via threaded holes 733 within one or more of the disks. Compression between the two disks, turns channels formed in a surface of the interface disk 503 into internal passages for directing fluid flow within the assembly 500. One example of channels within the interface disk 503 can be seen in the bottom view of FIG. 7B. In the device shown here, three channels 711, 712, 713 connect a mixer 715 with output passages from various passage groups. Additional channels have been included to provide connections between the various input passages, e.g. sample channel 721, water channel 722, acid channel 723, and reagent channel 724.

The rotor disk 501 can be connected with the stator disks (in this embodiment: the valve disk 502 and interface disk 503) in the valve cover 555 by a bolt 557 with a spring washer 558 inserted from the bottom of the disk 501 and a nut 559 placed on the top of the valve cover 555. The connection between these elements is such that the rotor disk is capable of being rotated about the vertical axis while maintaining a fluid seal between the elements. Accordingly, as with the sample preparation assemblies described above, openings 730 in the rotor disk face can be selectively aligned with channels within the valve disk 502, and thus passages within the interface disk 503. For example, in position 1 the channels can enable water, reagent, and acid to be drawn into the syringe pumps 510 in order to prepare a reagent blank. From position 2 the contents of the syringes, whether a reagent blank or sample solution, can be injected into the mixer. In position 3 the channels enable the sample, KI and acid to be drawn into the syringes in order to prepare a sample solution.

With reference to FIGS. 5A, 5B, 6B, and 6C, the syringe pumps 510 are each formed out of a generally cylindrical cavity formed within the rotor disk 501, and a plunger 570 inserted therein. The stems of the plungers 570 can be threaded and include a through-hole into which a guiding pin can be inserted. The guiding pin can prevent the rotation of the plunger as it moves up and down the cylindrical cavity. Each plunger cavity can accordingly include two guide groves to receive the guiding pin and allow it to ascend and descend. The vertical displacement of the threaded plunger 570 of each syringe pump can be controlled by rotating drive gears 572 having a central nut that receives the threaded end of the plunger 570. As the drive gears 572 rotate, the guiding pins 571 prevent the plungers from rotating along with them. The drive gears 572 can be press fit into ball bearing receivers 573, and each ball bearing receiver 573 can be secured in the corresponding cylindrical cavity of the rotor disk by a set screw inserted from the edge of the disk. Each of the syringe drive gears 572 can be driven by the rotation of a central gear 574 which is secured by another set screw to the axis of a first motor 575. For simplicity of calculation of rotation (which correlates with dispensed pump volume) a step motor can be used. Alternative embodiments can include the use of a DC motor which requires the addition of opto-couples for synchronization and counting the rotations of the motor. The step motor 575 can be secured to housing 576 with screws 577. The housing 576 is attached to the cylindrical surface of the rotor disk 501 and protects the step motor 575, drive gears 572, 574, and syringe assemblies.

The rotation of the rotor disk 501 relative to the stator disks 502, 503 can be enabled by a second motor 580 secured to the side of the cover 555. A gear 581 connected to the axel of the second motor 580 by another set screw, interlocks with the large gear teeth (visible, for example, in FIGS. 6B and 7D) on the outside of the rotor disk 501. This allows for alignment of the micropumps 510 within the rotor disk 501 with the various connections provided by the valve disk 502. In some embodiments, due to the requirement of only a limited angle of rotation of the rotor (e.g. sufficient rotation of $\theta_A$ plus $\theta_B$ degrees in the embodiment shown in FIG. 2C) in some embodiments, only a small portion of the outside of the rotor disk 501 needs to be geared.

Referring now primarily to FIGS. 5A-6B, the cover 555 has several openings corresponding with ports on the top surface of the interface disk 503. These ports can comprise needle ports for connecting solution bags as described above. For example, in a peracid monitor, the ports can include three needle ports 425, 426, 427. Each needle port can comprise a needle 425, 426, 427 secured by a nut 553. In such an example, these needle ports can be associated with connection to a source of reagent (e.g. KI) 423, a source of acid 422, and a source of water 424, such as the metalized bags previously discussed. In addition, the connection ports can comprise tubing connected with the sample preparation assembly. For example, sample tubing 428 can be connected to the interface layer 503 water-tightly with a nut 554 and a gasket 550.

With continued reference to FIGS. 5A-7B, in some embodiments, the optical cell can be connected directly to the interface layer. In particular, embodiments which include an integral mixer 511 such as that shown here can couple the optical cell or other sensor directly to the output of the integral mixer. The optical cell assembly can comprise a polyfluorocarbon tube 429 passing through a copper body 548. The sensor line 429 can be connected with the mixer outlet of the interface disk 503 with a gasket 550. A plastic thermal-insulating insert 549 can be used to separate the copper body 548 from cover 555. The copper body 548 includes a through-hole generally perpendicular to the main cell channel into which first and second optical fibers 436, 438 can be inserted. As described above, the first optical fiber 436 can transmit light from a light source (e.g. LED 435) and the second optical fiber can transmit light to a detector (e.g. photodiode 437). A temperature sensor 434 can be inserted into a slot in the top of the copper body 548. Thermo-electric Peltier modules 545 can be placed on the top surface of the copper body 548, above the through-hole. The Peltier modules 545 can be positioned adjacent the copper body 548 within a thermally insulating cutout 546. Accordingly, via control inputs 552 the Peltier modules 545 can be used to apply or remove heat from the copper body 548 (i.e. the optical cell) based upon feedback data from the temperature sensor 434. A thermal-insulating sleeve 531 can be slid around the whole optical cell assembly to further thermally isolate the cell. Additionally, a heat sink 560 can be affixed over the Peltier modules 545 secured to the copper body 548 by plastic screws 547. In certain embodiments of this design a mini fan with a brushless DC motor can be used to improve the efficiency of the Peltier modules 545.

As used herein, the term "peracid" refers to any acid that in which the hydroxyl group (—OH) is replaced with the peroxy group (—OOH). The peracid(s) may be C2-C18 peracid(s), such as C2 (peracetic) acid and C8 (peroctanoic) acid. It shall be understood that the apparatus and/or methods of the present invention may detect the combined presence of all peracids in a sample, whether the sample contains one or more than one different peracids, and that the invention is not limited in this respect.

Peroxycarboxylic acids generally have the formula $R(CO_3H)_n$. In some embodiments, the R may be an alkyl, arylalkyl, cycloalkyl, aromatic or heterocyclic group, and n may be one or two.

Peroxycarboxylic acids useful in this invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxysubric acid and mixtures thereof as well others known to those of skill in the art.

The concentrations of peracid and/or peroxide determined by use composition monitor may be used, for example, as feedback to controller to maintain the peracid concentration in the use composition within a predefined range and/or to cause the emptying of the use composition vessel and production of a new use composition when the hydrogen peroxide concentration exceeds the maximum peroxide threshold concentration. If, for example, the concentration of peracid in the use composition decreases below a predetermined level, the use composition may be replenished by adding a concentrated peracid composition to the use composition. As another example, if the concentration of peroxide in the use composition exceeds a predetermined level, the use composition may be replenished by emptying the use composition vessel of the spent use composition and generating a new use composition.

Use compositions including peracids and peroxides described herein may be used for a variety of domestic or industrial applications, e.g., to reduce microbial or viral populations on a surface or object or in a body or stream of water. The compositions may be applied in a variety of areas including kitchens, bathrooms, factories, hospitals, dental offices and food plants, and may be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces may be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces may be made from a variety of materials including, for example, paper, fiber, woven or nonwoven fabric, soft plastics and elastomers. The compositions may also be applied to soft surfaces such as food and skin (e.g., a hand). The use compositions may be employed as a foaming or nonfoaming environmental sanitizer or disinfectant.

The compositions may be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The compositions may also be used in veterinary products such as mammalian skin treatments or in products for sanitizing or disinfecting animal enclosures, pens, watering stations, and veterinary treatment areas such as inspection tables and operation rooms. The compositions may be employed in an antimicrobial foot bath for livestock or people.

The compositions may be employed for reducing the population of pathogenic microorganisms, such as pathogens of humans, animals, and the like. The compositions may exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens may cause a varieties of diseases and disorders, including Mastitis or other mammalian milking diseases, tuberculosis, and the like. The compositions may reduce the population of microorganisms on skin or other external or mucosal surfaces of an animal. In addition, the compositions may kill pathogenic microorganisms that spread through transfer by water, air, or a surface substrate. The composition need only be applied to the skin, other external or mucosal surfaces of an animal water, air, or surface.

The compositions may also be used on foods and plant species to reduce surface microbial populations; used at manufacturing or processing sites handling such foods and plant species; or used to treat process waters around such sites. For example, the compositions may be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions may be used to treat produce transport waters such as those found in flumes, pipe transports, cutters, slicers, blanchers, retort systems, washers, and the like. Particular foodstuffs that may be treated with compositions include eggs, meats, seeds, leaves, fruits and vegetables. Particular plant surfaces include both harvested and growing leaves, roots, seeds, skins or shells, stems, stalks, tubers, corms, fruit, and the like. The compositions may also be used to treat animal carcasses to reduce both pathogenic and non-pathogenic microbial levels.

The composition may be useful in the cleaning or sanitizing of containers, processing facilities, or equipment in the food service or food processing industries. The compositions may be used on food packaging materials and equipment, including for cold or hot aseptic packaging. Examples of process facilities in which the compositions may be employed include a milk line dairy, a continuous brewing system, food processing lines such as pumpable food systems and beverage lines, etc. Food service wares may be disinfected with the compositions. For example, the compositions may also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The compositions may also be used on or in other industrial equipment and in other industrial process streams such as heaters, cooling towers, boilers, retort waters, rinse waters, aseptic packaging wash waters, and the like. The compositions may be used to treat microbes and odors in recreational waters such as in pools, spas, recreational flumes and water slides, fountains, and the like.

A filter containing a composition may reduce the population of microorganisms in air and liquids. Such a filter may remove water and air-born pathogens such as *Legionella*.

The compositions may be employed for reducing the population of microbes, fruit flies, or other insect larva on a drain or other surface.

The compositions may also be employed by dipping food processing equipment into the use solution, soaking the equipment for a time sufficient to sanitize the equipment, and wiping or draining excess solution off the equipment. The compositions may be further employed by spraying or wiping food processing surfaces with the use solution, keeping the surfaces wet for a time sufficient to sanitize the surfaces, and removing excess solution by wiping, draining vertically, vacuuming, etc.

The compositions may also be used in a method of sanitizing hard surfaces such as institutional type equipment, utensils, dishes, health care equipment or tools, and other hard surfaces. The composition may also be employed in sanitizing clothing items or fabrics which have become contaminated. The composition is contacted with any contaminated surfaces or items at use temperatures in the range of about 4° C. to 60° C., for a period of time effective to sanitize, disinfect, or sterilize the surface or item. For example, the composition may be injected into the wash or rinse water of a laundry machine and contacted with contaminated fabric for a time sufficient to sanitize the fabric. Excess composition may be removed by rinsing or centrifuging the fabric.

The compositions may be applied to microbes or to soiled or cleaned surfaces using a variety of methods. These methods may operate on an object, surface, in a body or stream of water or a gas, or the like, by contacting the object, surface, body, or stream with a composition. Contacting may include any of numerous methods for applying a composition, such as spraying the composition, immersing the object in the composition, foam or gel treating the object with the composition, or a combination thereof.

The composition may be employed for bleaching pulp. The compositions may be employed for waste treatment. Such a composition may include added bleaching agent.

Other hard surface cleaning applications for the compositions include clean-in-place systems (CIP), clean-out-of-place systems (COP), washer-decontaminators, sterilizers, textile laundry machines, ultra and nano-filtration systems and indoor air filters. COP systems may include readily accessible systems including wash tanks, soaking vessels, mop buckets, holding tanks, scrub sinks, vehicle parts washers, non-continuous batch washers and systems, and the like.

Thus, embodiments of the valve analytical system are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims.

What is claimed is:

1. A rotary valve analytical system comprising:
a rotor having a rotor face, the rotor being rotatable about an axis perpendicular to the rotor face, wherein the rotor face has a plurality of openings, each of which is disposed at a selected radial distance from the axis, and wherein the openings extend into the rotor to form syringe barrels;
a stator disposed coaxially with the rotor, the stator having a stator face in sealable, slidable rotary contact with the rotor face, wherein the stator face has a plurality of sets of openings each set of openings comprising a plurality of openings disposed at a common radial distance from the axis and each set of openings having common angular distances separating the plurality of openings therein, wherein the common radial distance of each set of openings in the stator face equals one or more of the selected radial distances of the openings in the rotor face, and wherein each opening extends as a passage through the stator to an outlet port;
a plurality of plungers, one of said plungers disposed within each of the syringe barrels of the rotor;
a syringe drive motor, mechanically coupled with the plungers and adapted to drive and withdraw the plungers within the syringe barrels;
a rotor drive motor mechanically coupled with the rotor and adapted to cause the rotor to rotate relative to the stator;
a plurality of inlet tubes, each inlet tube coupled with one of the outlet ports of the stator and adapted to deliver a fluid to the system;
a plurality of outlet tubes, each outlet tube coupled with one of the outlet ports of the stator, wherein at least one opening of each set of openings of the stator is coupled with one of the outlet tubes and at least one opening of each set of openings of the stator is coupled with one of the inlet tubes;
a mixer in fluid communication with each of the outlet tubes and adapted to mix fluid that enters the mixer from the outlet tubes;
a sensor in fluid communication with the mixer, adapted to perform a measurement on the mixed fluids.

2. The rotary valve analytical system of claim 1, wherein the sensor comprises an optical sensor, the measurement comprising the measurement of one or more optical characteristics of the mixed fluids.

3. The rotary valve analytical system of claim 2, wherein the one or more measured optical characteristics of the mixed fluids are selected from the group comprising transmittance, absorbance, fluorescence, and time or temperature derivatives thereof.

4. The rotary valve analytical system of claim 3, wherein the one or more measured optical characteristics comprise absorbance and time derivative of absorbance.

5. The rotary valve analytical system of claim 1, wherein the plurality of inlet tubes comprise a sample inlet tube, coupled with a source of sample, a reagent tube coupled with a source of reagent, and an acid inlet tube coupled with a source of acid.

6. The rotary valve analytical system of claim 5, further comprising a diluent inlet tube coupled with a source of a diluent.

7. The rotary valve analytical system of claim 5, wherein the sample comprises a use composition comprising a peracid and a peroxide, the reagent comprises potassium iodide, and the acid comprises acetic acid.

* * * * *